United States Patent [19]
Karpf

[11] Patent Number: 5,915,240
[45] Date of Patent: Jun. 22, 1999

[54] COMPUTER SYSTEM AND METHOD FOR ACCESSING MEDICAL INFORMATION OVER A NETWORK

[76] Inventor: Ronald S. Karpf, 11425 Brandy Hall La., Gaithersburg, Md. 20878

[21] Appl. No.: 08/873,812

[22] Filed: Jun. 12, 1997

[51] Int. Cl.$^6$ .............................. G06F 17/30; G06F 7/00
[52] U.S. Cl. ............................ 705/2; 705/1; 395/200.33; 395/200.57
[58] Field of Search ....................... 705/2, 1; 395/200.33, 395/200.57

[56] References Cited

U.S. PATENT DOCUMENTS 5,694,596  12/1997  Campbell ................................. 395/610
5,764,916  6/1998   Busey et al. ........................ 395/200.57

*Primary Examiner*—Allen R. MacDonald
*Assistant Examiner*—Penny Caudle
*Attorney, Agent, or Firm*—Liniak, Berenato, Longacre & White LLC

[57] ABSTRACT

The invention is a Medical Lookup Reference computer system for accessing medical information over a network. The system partitions the functioning of the system between a client and server program in an optimal manner to assure synchronization of the master medical information databases on the servers with the local medical information database on the client, minimize the use of network resources, and allow new types of medical information to be easily included in the system. A server site on the network maintains a description of its medical information, as well as the most current and up-to-date medical reference information. The client program maintains a local database which is automatically synchronized over the network with revisions and new medical information, and provides a user with an interface to fully review the information in the database.

The system also uses a context-sensitive call facility so that users of the Medical Lookup Reference program can easily get further expert assistance about the medical topic. The call feature uses the network connection to establish a conversation between the user and a person at a help site specified by the type of medical information they are currently referencing. Once a connection is established, the system allows the user to engage in a conversation with the person at the help site, and a record of the conversation can be saved in a database for auditing purposes.

12 Claims, 23 Drawing Sheets

Fig. 8

Directory location
URL: http:/www.fred.net/adi

Source type
MedType: BldDrg  Blood Donor Disease Deferral Criteria
Query: al

| Term | Description | Type |
|---|---|---|
| » Albuterol | Yes, if not daily does for maintenance, but intermittent use. | BldDrg |
| » Alcopar | Defer 1 wk. after course completed and feel well. | BldDrg |
| » Aldochlor | Yes. | BldDrg |
| » Aldactone | Yes. | BldDrg |

Sunday, March 30, 1997 | Open | CAPS | NUM | ☎ | Qry: 26 | Sel: 4

Directory location
URL: http:/www.fred.net/adi

Source type
MedType: BldDrg  Blood Donor Disease Deferral Criteria
Query: al

| Term | Description | Type |
|---|---|---|
| » Albuterol | Yes, if not daily does for maintenance, but intermittent use. | BldDrg |
| » Alcopar | Defer 1 wk. after course completed and feel well. | BldDrg |
| » Aldochlor | Yes. | rg |
| » Aldactone | Yes. | rg |

Select All
DeSelect All

Clear
Print

Sunday, March 30, 1997 | Open | CAPS | NUM | ☎ | Qry: 26 | Sel: 4

— 920
— 910
— 940  930
900

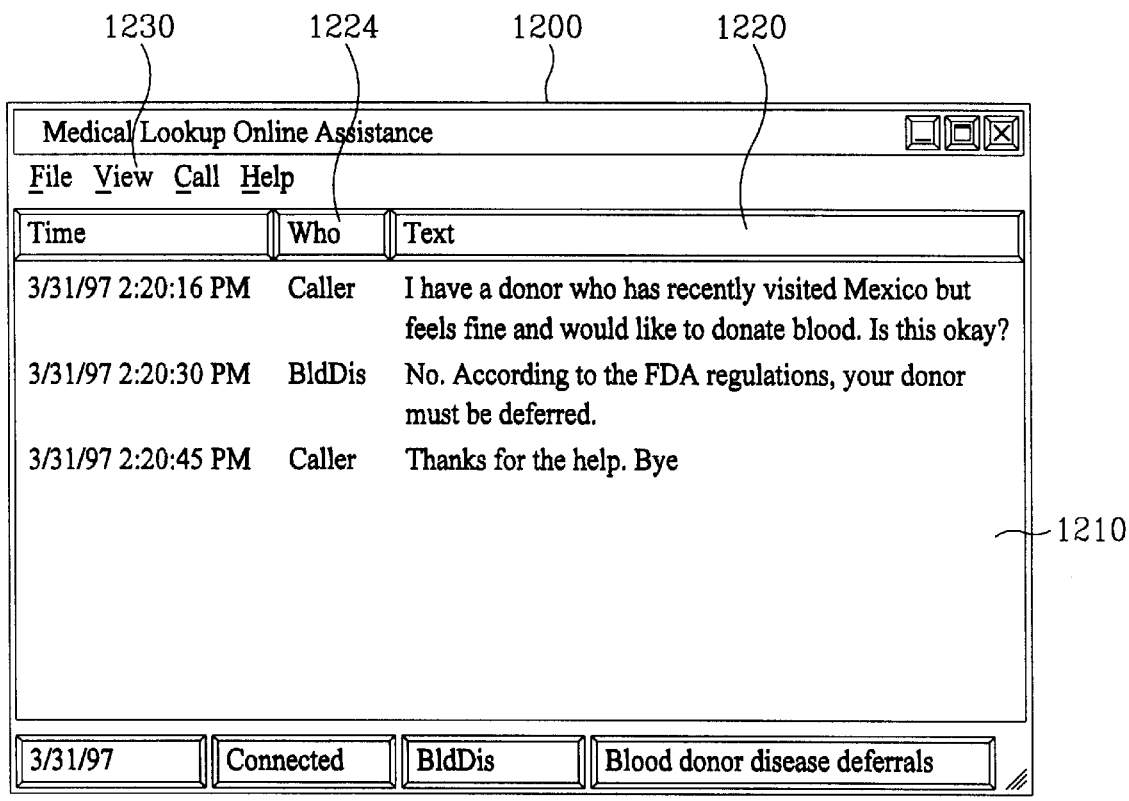

Fig. 14

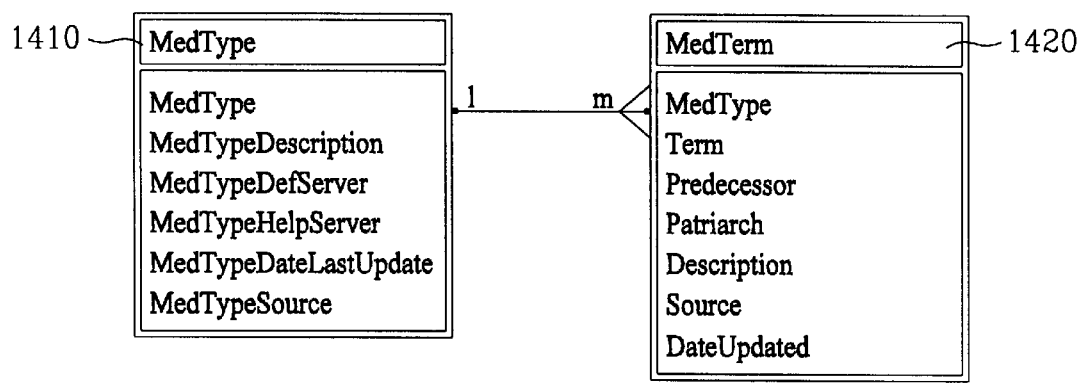

Fig. 15

Table: MedType

| # | Field | Attribute | |
|---|---|---|---|
| 1 | MedType | varchar (8) | 1510 |
| 1 | MedType | varchar (8) | |
| 2 | MedTypeDescription | varchar (60) | |
| 3 | MedTypeDefServer | varchar (128) | |
| 4 | MedTypeHelpServer | varchar (128) | |
| 5 | MedTypeDateLastUpdate | dd/mm/yyyy | |
| 6 | MedTypeSource | varchar (8) | |

Table: MedTerm

| # | Field | Attribute | |
|---|---|---|---|
|  |  |  | 1520 |
| 1 | MedType | varchar (8) | |
| 2 | Term | varchar (32) | |
| 3 | Predecessor | varchar (8) | |
| 4 | Patriarch | varchar (8) | |
| 5 | Description | varchar (255) | |
| 6 | Source | varchar (8) | |
| 7 | DateUpdated | dd/mm/yyyy | |

Table: Dialog

| # | Field | Attribute |
|---|---|---|
| 1 | DialogID | number |
| 2 | DateTimeStarted | dd/mm/yyyy:hh24:mi:ss |
| 3 | MedType | varchar (8) |
| 4 | CallerNetAddr | varchar (128) |
| 5 | CalleeNetAddr | varchar (128) |

Table: Messages

| # | Field | Attribute |
|---|---|---|
| 1 | DialogID | number |
| 2 | msgAuthor | 1=caller, 2=callee |
| 3 | msgID | number |
| 4 | DateTime | dd/mm/yyyy:hh24:mi:ss |
| 5 | msgText | varchar (2000) |

2100

| MedLkUp-client State | Network Message | MedCall-server State |
|---|---|---|
| MEDLKUP | setup MedCall → <br> ← AVAILABLE (if MedCall specialist is available) <br> ← UNAVAILABLE (if MedCall specialist is not available) | WAIT_FOR_CALL |
| MEDLKUP | any other message → <br> ← UNKNOWN REQUEST | WAIT_FOR_CALL |
| CALL | close or terminate connection → | TALK |
| CALL | ← close or terminate connection | TALK |
| CALL | send client-dialog → | TALK |
| CALL | ← send server-dialog | TALK |
| CALL | any other message → <br> ← unknown request | TALK |
| CALL | ← any other message <br> unknown request → | TALK |

| State | Operation | Action |
|---|---|---|
| | | State=INITIALIZE |
| START | StartUp | |
| INITIALIZE | initialize | if OpenDatabase fails then<br>  msgOperator "Database cannot be opened"<br>  State = END<br>elseif networkConnection is available then<br>  State = AUTO_UPDATE_DB<br>else<br>  State = MEDLKUP<br>endif |
| AUTO_UPDATE_DB | NetworkMessage | For each MedType in the MedType Table Do the Following Processing<br>Open connection with network server associated with MedType<br>if connection is opened successfully then<br>  Format a request-msg with asofdate parameter='dd/mm/yyyy'=date MedType lastUpdated<br>  Send request-msg<br>  if response-msg received successfully then<br>    close connection<br>    Begin Transaction<br>    if update MedDesc in database is successful then<br>      reset MedTypeDateLastUpdate = today<br>      commit<br>    else<br>      message on screen ('Could not update database')<br>      Rollback<br>    endif<br>  else<br>    close connection<br>    message on screen ('response not received')<br>  endif |

FROM FIG. 22A → TO FIG. 22C

| MEDLKUP 2240 | Initialize 2241 | else<br>  message on screen ('connection could not be opened')<br>endif<br>Loop<br>State = MEDLKUP<br><br>Initialize MedType combo box and other fields on screen from MedType database<br>Display QueryGrid<br>Set CurrentGrid = QueryGrid<br>Set current MedType = First entry in MedType combo box<br>State = MEDLKUP |
|---|---|---|
| | User-request 2242 | Wait for User-request<br>Select Case User-request<br>  Case SELECT_MEDTYPE<br>    Change Value of MedType Variable to that selected in combo box<br>    State = MEDLKUP<br>  Case SELECT_QUERY_GRID<br>    Display QueryGrid<br>    Set CurrentGrid = QueryGrid<br>    State = MEDLKUP<br>  Case SELECT_SELECTION_GRID<br>    Display SelectionGrid<br>    Set CurrentGrid = SelectionGrid<br>    State = MEDLKUP<br>  Case KeyEnter<br>    If field is QueryField then<br>      If KeyPressed = ENTER<br>        Display and clear QueryGrid<br>        Perform search in database and display results in QueryGrid<br>        Set CurrentGrid = QueryGrid |

Fig. 22C

```
        else
            add keyvalue to current field
        endif
        State = MEDLKUP
    elseif field is URL then
        if KeyPressed = ENTER
            Set MedTypeServer to value of URL field
            Set asofDate = '01/01/1950'
            State = NEW_MEDTYPE
        else
            add key value to current field
            State = MEDLKUP
        endif
    endif
Case CLEAR
    Clear the contents of the CurrentGrid
    State = MEDLKUP
Case PRINT
    Print the contents of the CurrentGrid
    State = MEDLKUP
Case CALL
    If network is available then
        Connect with MedTypeHelpServer associated with current MedType
            if connection with MedTypeHelpServer is 'AVAILABLE' then
                State = CALL
            else if response-msg = 'UNAVAILABLE' then
                message on screen ('Cannot connect to Help site')
                State = MEDLKUP
            endif
    else
```

Fig. 22D

```
                    message on screen ('Network not available')
                    State = MedLkUp
                  endif
                Case UpdateMedType
                    State = UPDATE_MEDINFO
                Case Exit
                    State = CLOSEDB
              EndSelect
```

| | NetworkMessage | Open connection with network server associated with MedType<br>if connection is opened successfully then<br>  Format a request-msg for MedType-list<br>  Send request-msg<br>  if response-msg received successfully then<br>    close connection<br>    Begin Transaction<br>    if update MedType in database is 'UNAVAILABLE'<br>      Rollback<br>      message on screen ('Update invalid')<br>      State = MEDLKUP<br>    else<br>      Set MedTypeParm = New MedType<br>      State = UPDATE MEDINFO<br>    endif<br>  elseif response-msg = 'UNAVAILABLE' then<br>    close connection<br>    message on screen ('Server UNAVAILABLE')<br>    End Transaction<br>    State = MEDLKUP<br>  endif |
|---|---|---|
| NEW MEDTYPE<br>~2250 | | |

Fig. 22E

| | | |
|---|---|---|
| UPDATE_MEDINFO 2260 | NetWorkMessage | Format a request-msg with asofdate parameter<br>Send request-msg<br>if response-msg received successfully then<br>    close connection<br>    Begin Transaction<br>    if update MedDesc in database is successful then<br>        commit<br>    else<br>        message on screen ('Could not update database')<br>        Rollback<br>    endif<br>elseif response-msg = 'UNAVAILABLE' then<br>    close connection<br>    message on screen ('Server UNAVAILABLE')<br>endif<br>State = MEDLKUP |
| CALL 2270 | StartCall 2271 | Start MedCall Program, display screen in SplitScreen View<br>clear msgbuffer<br>Start capture of dialog to database |
| | NetworkMessage 2272 | Get and parse message<br>if msg-type =talk then<br>    display response on screen<br>    save response on screen<br>else<br>    discard response-msg<br>endif<br>State = CALL |
| | UserAction 2273 | Wait for user-request<br>Select Case User-request |

FROM FIG. 22D

```
                    Case KeyPressed
                        if keypressed = ENTER then
                            send msgbuffer to MedCall-server
                            write msgbuffer to dialog database
                            clear msgbuffer for next message
                        else
                            add keypressed to msgbuffer
                            display msgbuffer on screen
                        endif
                        State = CALL
                    Case Print
                        print entire dialog
                        State = CALL
                    Case SPLITSCREEN
                        Display dialog on screen in SplitScreen View
                        State = CALL
                    Case DIALOGSCREEN
                        Display dialog on screen in DialogScreen View
                        State = CALL
                    Case EXIT, BYE
                        Close connection with MedCall-server
                        Write end-message
                        Commit all help dialog to database
                        Terminate MedCall program
                        State = MEDLKUP
                    End Select
```

| CLOSEDB | CloseDatabase | CloseDatabase<br>State = END |
| --- | --- | --- |
| END | End processing | Stop MedlkUp-client r program |

2280

2290

FROM FIG. 22E

Fig. 23

| State | Operation | Action |
|---|---|---|
| START | StartUp | • State=INITIALIZE |
| INITIALIZE 2320 | initialize | • if OpenMedicalDataBase fails then<br>    msgOperator "Database cannot be opened"<br>    State = END<br>  else<br>    State = WAIT_FOR_REQ<br>  endif |
| WAIT_FOR_REQ 2330 | NetworkRequest 2331 | • Wait for a request-msg from a MedLkUp-client<br>• When request-msg received establish connection with MedLkUp-client<br>• If request-msg is for a MedType-defination<br>    send MedType.1st file<br>  elseif request-msg is for a MedicalDictionary-entries then<br>    parse request-msg for MedType and asof-request-date<br>    retrieve and format response-msg for all entries in medical database entered or<br>        updated since date = 'mm/dd/yyyy'<br>    send response-msg<br>  else<br>    discard request-msg<br>    send response-msg = 'UNKNOWN REQUEST'<br>  endif<br>• close connection with MedLkUp-client<br>• State = WAIT_FOR_REQ |
| | TerminateServer 2332 | • State = CLOSEDB |
| CLOSEDB | CloseDatabase | • CloseMedicalDatabase<br>• State = END |
| END 2350 | End processing | • Stop server program |

| State | Operation | Action |
|---|---|---|
| START | StartUp | • State=INITIALIZE |
| INITIALIZE<br>2420 | initialize | • if OpenConversationDataBase fails then<br>   msgOperator "Database cannot be opened"<br>   State = END<br>  else<br>   State = WAIT_FOR_REQ<br>   Set MedInfoSpecialistAvailable = true<br>   Set NumLiveCalls = 0<br>  endif |
| WAIT_FOR_CALL<br>2430 | NetworkRequest<br>2431 | • Wait for a request-msg from MedLkUp-client<br>• If request-msg is to establish a MedCall then<br>   Write request-msg to conversationDatabase<br>   Establish connection with MedLkUp-client<br>  • If MedInfoSpecialistAvailable = false then<br>    send response-msg = "UNAVAILABLE" to MedLkUp-client<br>    write OpsUnavailable-msg to ConversationDatabase<br>    terminate connection with MedLkUp-client<br>    State = WAIT_FOR_CALL<br>  else<br>    send response-msg = "AVAILABLE" to MedLkUp-client<br>    write OpsAvailable-msg to ConversationDatabase<br>    MedInfoSpecialistAvailable = false<br>    NumLiveCalls = 1<br>    Set TalkBuffer = ""<br>    State = TALK<br>  endif<br>else<br>   discard request-msg<br>   send response-msg = 'UNKNOWN REQUEST' to MedLkUp-client<br>   State = WAIT_FOR_CALL<br>endif |

FROM FIG. 24A →

← TO FIG. 24C

| | | |
|---|---|---|
| SetOpsUnavailable 2432 | • if MedInfoSpecialistAvailable = true then<br>   MedInfoSpecialistAvailable = false<br>  endif<br>• State = WAIT_FOR_CALL | |
| SetOpsAvailable 2433 | • if MedInfoSpecialistAvailable = false then<br>   MedInfoSpecialistAvailable = true<br>  endif<br>• State = WAIT_FOR_CALL | |
| 2434 — TerminateServer | • State = CLOSEDB | |
| TALK 2440 | NetworkRequest 2441 | • Wait for request-msg from MedLkUp-client<br>• if request-msg is to closeConnection-msg then<br>   write closeConnection-msg to ClientPanel on Screen<br>   write closeConnection-msg to ConversationDatabase<br>   close connection with MedLkUp-client<br>   MedInfoSpecialistAvailable = true<br>   NumOpenLines = 0<br>   clear ClientPanel and ServerPanel on Screen<br>   State = WAIT_FOR_CALL<br>  elseif request-msg is talk-msg then<br>   write talk-msg to ClientPanel on screen<br>   write talk-msg to ConversationDatabase<br>   State = TALK<br>  elseif request-msg is terminate-call then<br>   write terminate-msg to ClientPanel on Screen<br>   write terminate-msg to ConversationDatabase<br>   close connection with MedLkUp<br>   MedInfoSpecialistAvailable = true<br>   NumOpenLines = 0<br>   clear ClientPanel and ServerPanel on Screen<br>   State = WAIT_FOR_CALL |

Fig. 24C

FROM FIG. 24B

| | | |
|---|---|---|
| | | else<br>  discard request-msg<br>  State = TALK<br>endif |
| | KeyPressed<br>2442 | • if keypressed = ENTER key then<br>  send TalkBuffer to MedLkUp-client<br>  write TalkBuffer to ConversationDatabase<br>  Set TalkBuffer = ""<br>  State = TALK<br>else<br>  TalkBuffer = TALKBuffer & keyPressed<br>  State = TALK<br>endif |
| | SetOpsUnavailable<br>2443 | • if MedInfoSpecialistAvailable = true then<br>  MedInfoSpecialistAvailable = false<br>  send OpsTemporarilyUnavailable-msg to MedLkUp-client<br>  write OpsTemporarilyUnavailable-msg to ConversationDatabase<br>endif<br>• State = TALK |
| | SetOpsAvailable<br>2444 | • if MedInfoSpecialistAvailable = false<br>  MedInfoSpecialistAvailable = true<br>  send OpsNowAvailable-msg to MedLkUp-client<br>  write OpsNowAvailable-msg to ConversationDatabase<br>endif<br>• State = TALK |
| | TerminateServer<br>2445 | • send OpsMustTerminate-msg to MedLkUp-client<br>  write OpsMustTerminate-msg to ConversationDatabase<br>  close connection with MedLkUp-client<br>  State = END |
| CLOSEDB<br>2450 | CloseDatabase<br>2460 | • Close ConnectionDatabase<br>• State = END |
| END | End processing | • Stop server program |

COMPUTER SYSTEM AND METHOD FOR ACCESSING MEDICAL INFORMATION OVER A NETWORK

BACKGROUND OF THE INVENTION

1. Field of the Invention

This invention relates to a computer system and method for accessing medical information organized by medical topic over a network. Each medical topic may be organized in a hierarchical structure and is stored on a database server computer containing the medical dictionary. The medical information is accessed from a client computer on the network and contains its own local version of the medical dictionary. The invention provides a better means to synchronize information on the two computers, allows access to multiple different medical dictionaries located on different servers, makes it easy to add new medical dictionaries, and minimizes the usage of network resources while achieving these goals.

The system also uses a context-sensitive call facility so that users of the medical information system can utilize the computer network to get immediate assistance directly related to the information they are accessing. At any time during the use of the system, the user may begin a completely audited conversation over the computer network with persons at a help server site that have in-depth knowledge of the medical information source that is being referenced.

2. Description of the Prior Art

Computer systems to provide a readily accessible means to reference and lookup medical information are ubiquitous throughout the industry. They span the range from simple single-user systems running on workstations and personal computers to complicated multi-user database systems. The five characteristics of these systems that we are concerned with in this invention are; (1) the means by which the medical information is disseminated (2) the means by which the medical information is maintained up-to-date (3) the scope of the different types of medical information they cover and, (4) how assistance in the use of the program and the medical information is provided to the user (5) how an audit record of assistance that is provided to the user is maintained.

Approaches to these problems vary widely. In many systems the medical information is provided on CD-ROM, disk, or other fixed medium, along with a computer program that has the means to search, display, print and otherwise use this information. Such a computer program may also provide on-line or other help facility to assist the user with use of the program and using the medical information. Delivering the medical information on fixed medium has serious problems though, as the information can only be as current as when the fixed medium was produced, and the included help facility may not address all questions the user may have. In many situations however Medical information must be up-to-date and current, as when its use is regulated by law as is the case with blood donor deferral criteria, or in cases when physicians will use a medical database to reference the latest patient treatment protocols as they do with cancer treatment protocols that may determine in part the treatment selected. In these cases, such fixed systems are inadequate. Those systems that attempt to address the timeliness of the data with frequent data updates are difficult to manage and require actions by the user to keep the database up-to-date.

Other systems use network connections to a central database facility to address the timeliness of the information. In these systems the central database is maintained with current and up-to-date information which the user accesses. These systems however, also have their limitations. The network connections are persistent connections requiring the expenditure of significant network and computer resources, usually host-based systems, operating from a terminal with a separate computer session executing on a central machine, requiring expenditure of the central computer's resources to deliver the information. These systems also suffer from the problem that the scope of the information coverage is limited and information from other single-user or central database systems cannot be accessed from the same user-interface program. Many of these systems will provide computer help facilities but are limited to on-line textual materials.

The ability of the user to acquire assistance in the use of the database system, or on the content and use of the medical information, varies from little, to those systems that provide on-line textual help, to those systems that provide phone-in help desks, manned by persons who are expert in the systems and information that they support. Both of these approaches have drawbacks. The on-line textual systems, may not have sufficient information content to address all the user questions, and if it does the user may have difficulty getting the assistance they require. Telephone help lines suffer from the problem that the user must have access to a phone. Often even if a phone is available it is not readily accessible to the user within proximity of the computer system, so that the user can have access to the phone help and the computer system at the same time. Another serious drawback is that at best written logs or notes are maintained about the conversation, decision, and actions taken, but in many medical situations, such as when medical historians may be interviewing prospective blood donors to determine their eligibility to donate blood, and may need to phone or otherwise talk to the medical director for this determination, a more substantial record is desirable, or even required by state or federal regulatory agencies.

OBJECT AND ADVANTAGES OF THE INVENTION

In accordance then with the purpose of the invention, as embodied and broadly described herein, the inventions consists of an medical lookup client programs running on a client node of a computer network, a multiplicity of medical lookup server programs running on server nodes of a computer network, and a multiplicity of medical call server programs running on other server node of the computer network. For clarity, the medical lookup client program will be referred to as a MedLkUp-client, the medical lookup server program referred to as a MedLkUp-server, and the medical call server will be referred to as a MedCall-server.

Each MedLkup-server provides a central database for a single type of medical information, and the MedLkUp-client program maintains a local database of medical information for a multiplicity of types of medical information. The MedLkUp-client program automatically updates itself from the MedLkUp-servers, over the network whenever it is started assuring the user that the information is always up-to-date. The system also allows the user to attach new medical information automatically by specifying the network address of the MedLkUp-server. The connection between the MedLkUp-client and the MedLkUp-server is a non-persistent connection, maintained only for the duration of the time necessary to access the medical information, assuring that a minimum of network and database resources are necessary to maintain the currency of the information. Since the MedLkUp-client can access and maintain information contained on multiple MedLkUp-servers, information from diverse medical sources can be contained in the same local database.

Finally, the system uses a network chat facility, referred to as a MedCall, which allows the user to engage in a real-time keyboard-entered and typed conversation using the network, between the user of the MedLkUp-client and a person at a help site who can provide expert assistance to the user. The network connections are maintained only for the length of a typed conversation to minimize network resources. This provides a superior alternative to phone-call type of help desks, and to on-line text help facilities as a means for the user to acquire help about the medical information they are attempting to use. In this circumstance a complete textual record of the typed dialog between the persons using the MedLkUp-client and the MedCall-server may be maintained in a database.

Other objects and advantages of the invention will be set forth in part in the description which follows and in part will be obvious from the description or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, which are incorporated in and constitute a part of the specification, illustrate the preferred embodiment of the invention, and together with the detailed description of the preferred embodiment, serve to explain the principles of the invention.

FIG. 8 is an example of a screen of the MedLkUp-client showing the display of selected items of medical information.

FIG. 9 is an example of a screen of the MedLkUp-client showing a popup context menu with operations that can be performed on the display of medical information.

FIG. 12 is an example of a MedCall conversation in dialog view.

FIG. 13 is a file description of MedType.1st describing the information contained in a medical dictionary central database.

FIG. 14 is an entity-relations diagram of the medical dictionary database used on the MedLkUp-client and MedLkUp-server.

FIG. 15 displays the table structures for the medical dictionary database.

FIG. 21 displays the message protocols for the MedLkUp-client communication with the MedCall-server.

FIG. 22 is a state table describing the operation of the MedLkUp-client program.

FIG. 23 is a state table describing the operation of the MedLkUp-server program.

FIG. 24 is a state table describing the operation of the MedCall-server.

DETAILED DESCRIPTION OF THE PREFERRED EMBODIMENT

References will now be made in detail to the preferred embodiments of the invention, examples of which are illustrated in the accompanying drawings. Wherever possible, the same reference numbers will be used throughout the drawings to refer to the same or like parts.

1. Overview

This invention is a computer system for providing up-to-date medical information over a network. The system partitions the operation of the system between a MedLkUp-client program which is the program that the user operates to access the medical information, and server programs that provide information and services to the user of the MedLkUp-client. A MedLkUp-server program maintains a central and up-to-date medical dictionary database that the MedLkup-client uses to automatically update its local database at startup. During a MedLkUp-client session, new MedLkUp-servers can be accessed over the network to add new types of medical information to its local database. All communication between the MedLkUp-client and MedLkUp-server use a non-persistent network connection maintained only for the duration of the transaction.

Also, the sources of medical information can provide users of the MedLkUp-client access to experts available to answer questions through a fully audited MedCall chat facility. The MedCall-client can connect to a MedCall-server over the computer network and engage in a two-way typed conversation. All communications between the client and server sides of the system are through connections that are maintained and persist only for the length of time required for the conversation.

The MedLkUp-client then consists of a computer program, its database and the messaging protocol used to communicate with the MedLkUp-server over the network. The MedLkUp-server consists of a computer program, its database, descriptive file, and the messaging protocols to communicate with the MedLkUp-client over the network. The MedCall-server consists of a computer program, its database and the messaging protocol used to talk with the MedLkUp-client over the computer network. The programs, databases, and messaging protocols that constitute the system are described in detail in the sections that follow.

2. A System and Method for Accessing Medical Information Over a Network

A. Hardware, Operating System and Application Development Software

Figure 1:
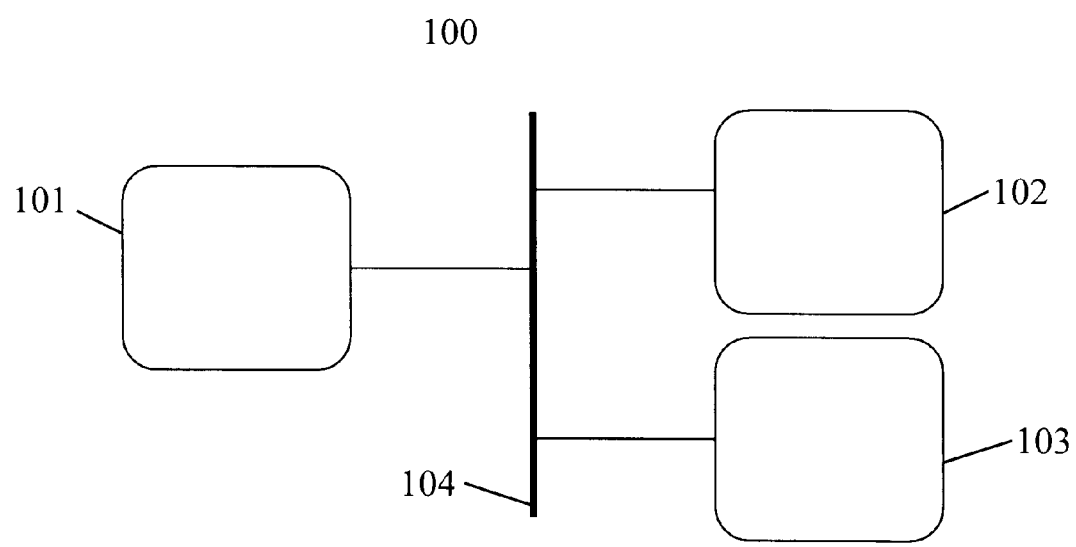
FIG. 1 is a block diagram of the preferred embodiment of the present invention.

FIG. 1 is a block diagram of a preferred embodiment of the present invention. A system 100 of FIG. 1 illustrates the MedLkUp-client computer 101, the MedLkUp-server computer 102, the MedCall-server 103, and the computer network 104 over which the MedLkUp-client and the MedLkUp-server establish communication, and the MedLkUp-client and the MedCall-server establish communication. In the preferred embodiment the computer network is an industry standard ethernet, and an industry standard TCP/IP network protocol.

Figure 2:
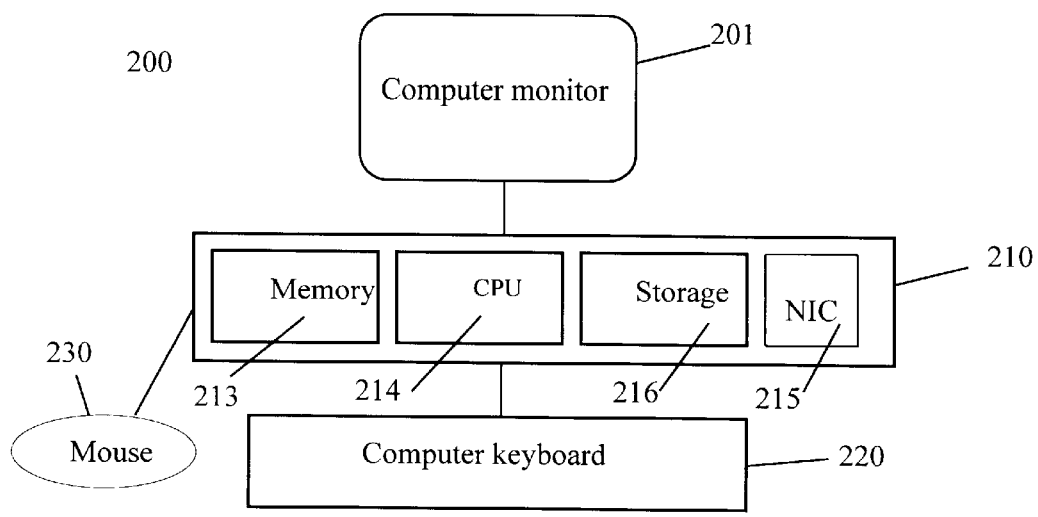
FIG. 2 is a block diagram of the Medlkup-client of FIG. 1.

FIG. 2. is a more detailed block diagram of the MedLkUp-client computer 101 of FIG. 1. In the preferred embodiment the system 200 consists of a computer monitor 201, a computer 210, a computer mouse 230, and a computer keyboard 220. The computer 210 includes a memory 213 and a processor (CPU) 214, a mass storage device 216, and a network interface card (NIC) 215. Monitor 201, the computer mouse 230, and computer keyboard 220, are connected to computer 210 in a manner known to persons of ordinary skill in the art.

Computer 210 preferably is a Dell OptiPlex XMT, the keyboard 220 is a Dell Quietkey, and monitor 201 a Dell Ultrascan 17XE, all manufactured by the Dell Corporation of Austin, Tex. The NIC 215, is an Intel EtherExpress 16, 16-bit ISA ethernet Adapter card manufactured by the Intel Corporation of Santa Clara, Calif. The computer mouse 230, is a Microsoft System Mouse, manufactured by the Microsoft Corporation of Redmond, Wash.

In the preferred embodiment, computer 210 is executing under Microsoft Windows 95. The MedLkUp-client program is written in a computer language called Microsoft Visual Basic using the Microsoft Visual Basic Version 4.0 Professional Edition, and the Microsoft HTTP Client Control, Version 5.00.2823, and the Microsoft Winsock TCP Control, Version 5.00.2823. The medical dictionary database is stored in a Microsoft Access Version 2.00 database. The MedCall database is also saved in the Microsoft Access database. These application development tools are from the Microsoft Corporation of Redmond, Wash. Other embodiments may use other hardware and software components.

Figure 3:
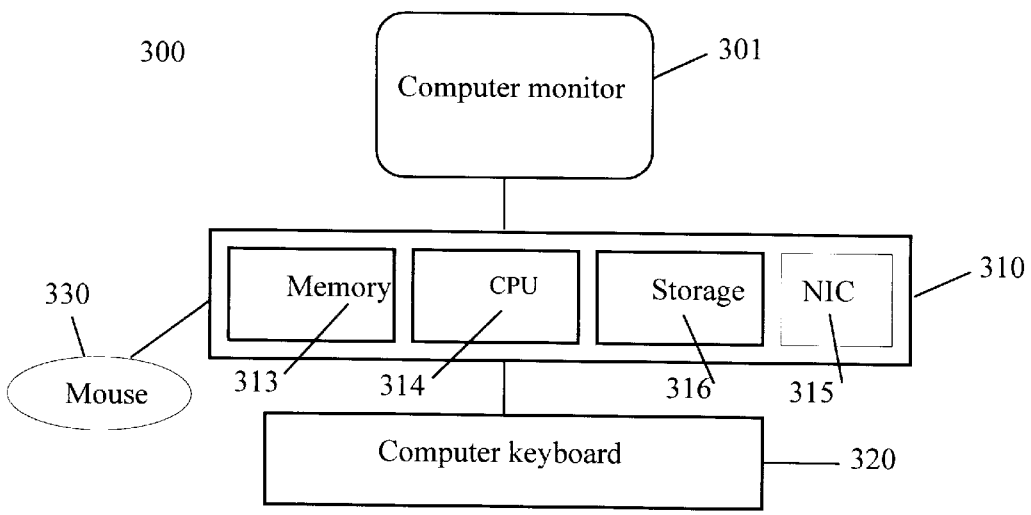
FIG. 3 is a block diagram of the Medlkup-server of FIG. 1.

FIG. 3. is a more detailed block diagram of the MedLkUp-server computer 102. In the preferred embodiment the system 300 consists of a computer monitor 301, a computer 310, a computer mouse 330, and a computer keyboard 320. The computer 310 includes a memory 313 and a processor (CPU) 314, a mass storage device 316, and a network interface card (NIC) 315. Monitor 301, the computer mouse 330, and computer keyboard 320, are connected to computer 310 in a manner known to persons of ordinary skill in the art.

Computer 310 preferably is a Dell OptiPlex XMT, the keyboard 320 is a Dell Quietkey, and monitor 301 a Dell Ultrascan 17XE, all manufactured by the Dell Corporation of Austin, Tex. The NIC 315, is an Intel EtherExpress 16, 16-bit ISA ethernet Adapter card manufactured by the Intel Corporation of Santa Clara, Calif. The computer mouse 330, is a Microsoft System Mouse, manufactured by the Microsoft Corporation of Redmond, Wash.

In the preferred embodiment, computer 310 is executing under Microsoft Windows NT Server 3.51, and is running the Microsoft Internet Information Server. The MedType.1st file is stored on the MedLkUp-server, and the medical definition database is stored on the MedLkUp-server in a Microsoft Access Version 2.00 database. The MedLkUp-server uses the Microsoft Internet Information Server, and the interface to the Access database is written following the industry standard Common Gateway Interface (CGI) in Microsoft Visual Basic. All four products are manufactured by the Microsoft Corporation of Redmond, Wash. Other embodiments may use other hardware and software components.

Figure 4:
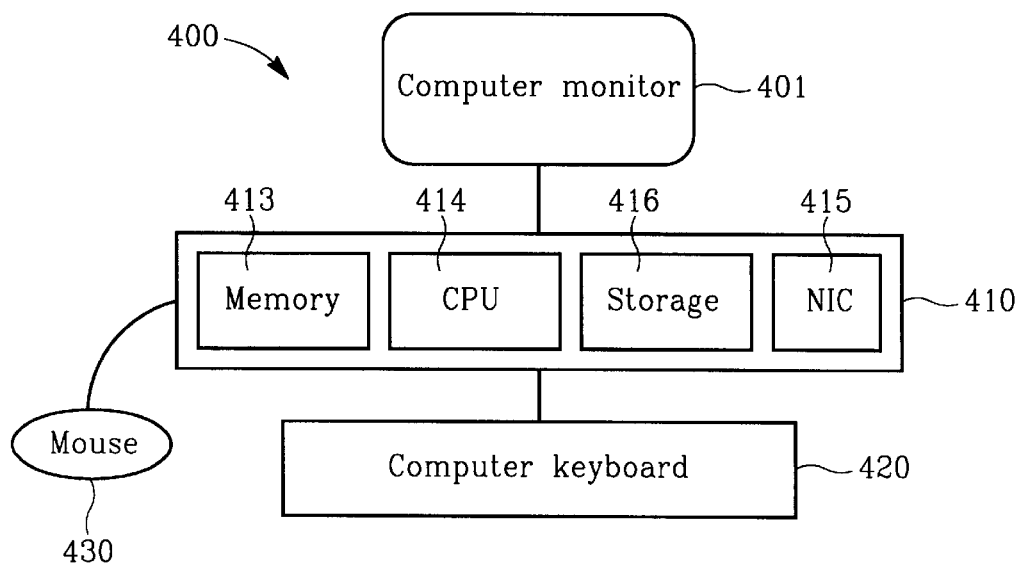
FIG. 4 is a block diagram of the MedlCall-server of FIG. 1.

FIG. 4. is a more detailed block diagram of the MedCall-server computer 103. In the preferred embodiment the system 400 consists of a computer monitor 401, a computer 410, a computer mouse 430, and a computer keyboard 420. The computer 410 includes a memory 413 and a processor (CPU) 414, a mass storage device 416, and a network interface card (NIC) 415. Monitor 401, the computer mouse 430, and computer keyboard 420, are connected to computer 410 in a manner known to persons of ordinary skill in the art.

Computer 410 preferably is a Dell OptiPlex XMT, the keyboard 420 is a Dell Quietkey, and monitor 401 a Dell Ultrascan 17XE, all manufactured by the Dell Corporation of Austin, Tex. The NIC 415, is an Intel EtherExpress 16, 16-bit ISA ethernet Adapter card manufactured by the Intel Corporation of Santa Clara, Calif. The computer mouse 430, is a Microsoft System Mouse, manufactured by the Microsoft Corporation of Redmond, Wash.

Figure 5:
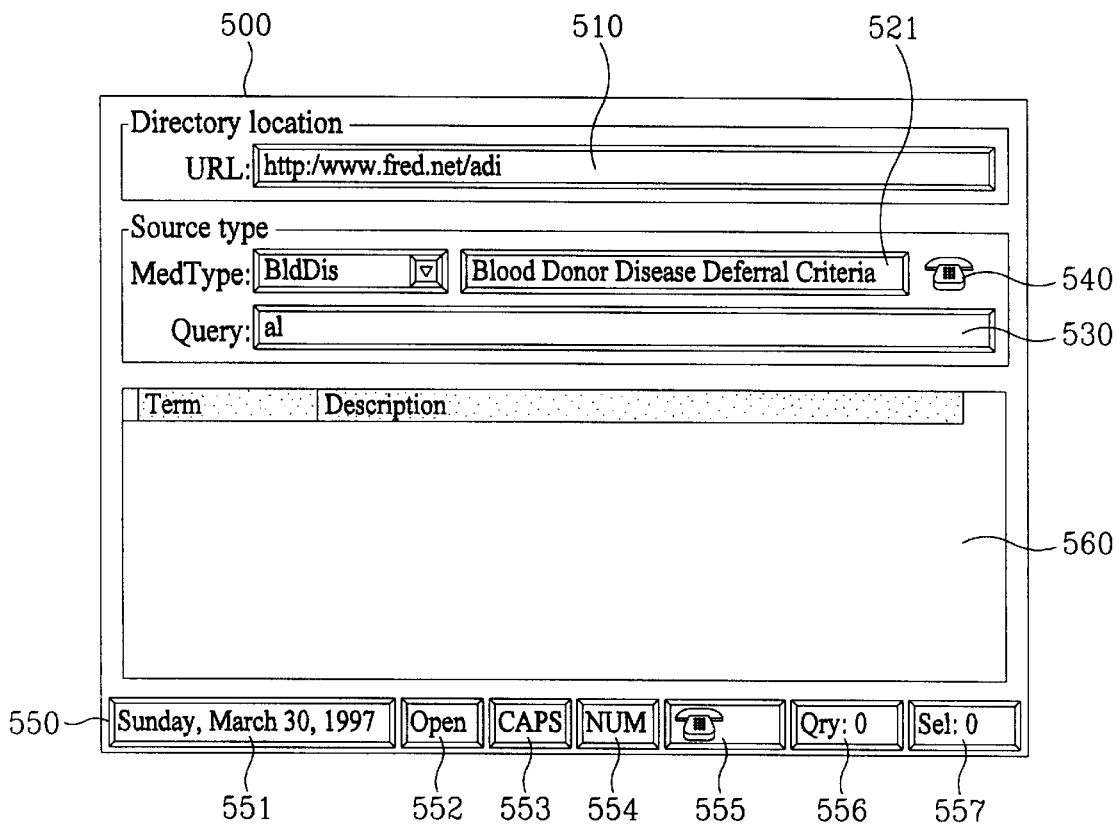
FIG. 5 is an example of the startup screen of the MedLkup-client program of FIG. 2.

In the preferred embodiment, computer 410 is executing under Microsoft Windows NT Server 3.51. The MedCall database is stored on the MedCall-server in a Microsoft Access Version 2.00 database, and the MedCall-server program is written in Microsoft Visual Basic and uses the Microsoft Winsock TCP Control, Version 5.00.2823. All four products are manufactured by the Microsoft Corporation of Redmond, Wash. Other embodiments may use other hardware and software components B. Screen formats—MedLkUp-client startup screen FIG. 5. is an example of the main screen 500 that is presented to the user on the display screen 201 of the MedLkUp-client of FIG. 2. It shows a drop-down combobox 520 which has an abbreviation for the currently chosen type of medical information (MedType) that the system will reference. A full description of the MedType is given in the label box 521. The text box 510 gives the network location of the MedLkUp-server for the MedType displayed in the combobox 520. This network location contains the MedType.1is file that describes the medical information contained on the server, and the medical dictionary central database with the most currently available information for the data source.

The textbox 530 provides the user with a means to enter a search term that will be used to retrieve records from the medical dictionary for the type of information specified by MedType. If the blinking cursor is not already focused on this textbox, then the mouse device is used to point and click at the box to set the program focus on this field. The keyboard is then used to type enter the search criteria. The figure shows that the portion of a search term 'al' has been entered, which when retrieval of information from the database is initiated, will result in all records from the 'BldDis' database that meet this criteria being retrieved from the database and displayed within the display grid. The display grid 560 is shown as it appears when the MedLkUp-client is first started up before any records have been retrieved from the database, or when 0 records meet the criteria and no records have been retrieved from the medical database associated with 'BldDis2 . It has column headings for 'Term', the term that is to be defined, and the description or definition of that term.

Along the bottom of the screen is a statusBar 550. The status bar has 7 fields. The first field 551, gives the day and date on which the current invocation of the MedLkUp-client was begun. Field 552 shows the status of the database, either open or closed. Field 553 displays the keyboard status of the 'Caps Lock' keyboard key. If it is grayed out, as shown on the figure then the 'Caps Lock' key has not been engaged and keyboard entries are in lower case unless the user also holds down the 'Caps Lock' key. If the field is not grayed out, then the 'Caps Lock' is engaged and keyboard entries are in upper case unless the user also holds down the 'Caps Lock' key. Field 554 displays the status of the 'Num Lock' keyboard key. If it is grayed out, as shown on the figure then the 'Num Lock' key has not been engaged and depressing a key on the numeric keyboard enters the corresponding cursor movement commands. If the 'Num Lock' key is not grayed out then the 'Num Lock' key is engaged and depressing a key on the numeric enters the corresponding number.

Field 555 on the statusbar 550 is used to initiate a MedCall with a MedCall-server site providing assistance in the operation of the MedLkUp-client program. The user selects this option by pointing and clicking at the 'telephone' icon with the mouse pointing device.

Field 540 provides the user with another way to access a MedCall-server site. Selecting this option, by pointing and clicking with the mouse pointing devices, will initiate a MedCall to a help site associated with the MedType displayed in field 520. This is a feature that allows the user to access on-line context-sensitive help from a site on the network providing expert assistance about the type of medical information they are currently accessing—in this case about 'Blood Donor Disease Deferral Criteria'. Field 556 on the statusbar 550 show the number of items that have been retrieved by the most recent database query, and Field 557 displays the number of items from the query that have been selected. These last two fields, 556 and 557, also serve as program buttons. Pointing and clicking at fields 556 or 557, cause the program to display the set of records retrieved by the most recent query or the set of selected records, respectively.

Figure 6:
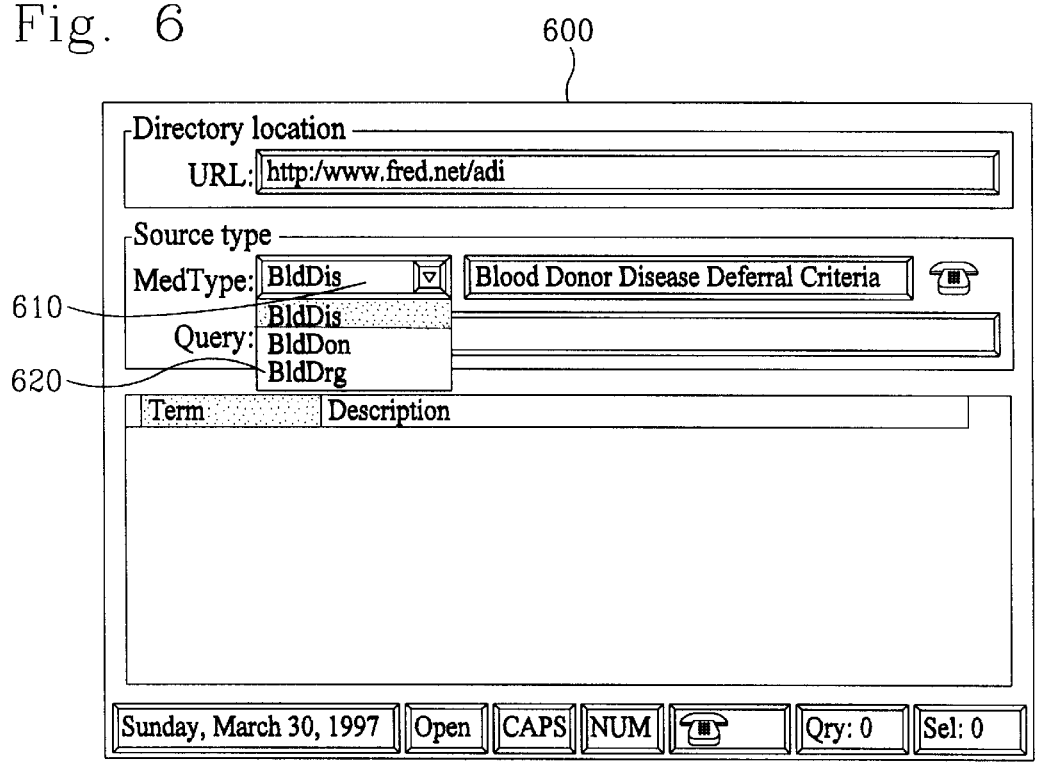
FIG. 6 is an example of a screen of the MedLkUp-client showing the selection of medical type.

FIG. 6. is an example of a screen 600 showing how the user selects the type of medical information on the display screen 201 of the MedLkUp-client of FIG. 2. It shows a drop-down combobox 610 after the user has pointed and clicked on the combobox 'down-arrow', which causes the combobox to present all types of medical information presently stored in the database in a listing 620, and from which the user may select. The MedType is chosen from the combobox by the user by pointing at an entry in the list. As the user points at a list entry it is shown in reverse video, and is selected by clicking on this entry with the mouse. This cause the chosen entry to be displayed in the field 610.

Figure 7:
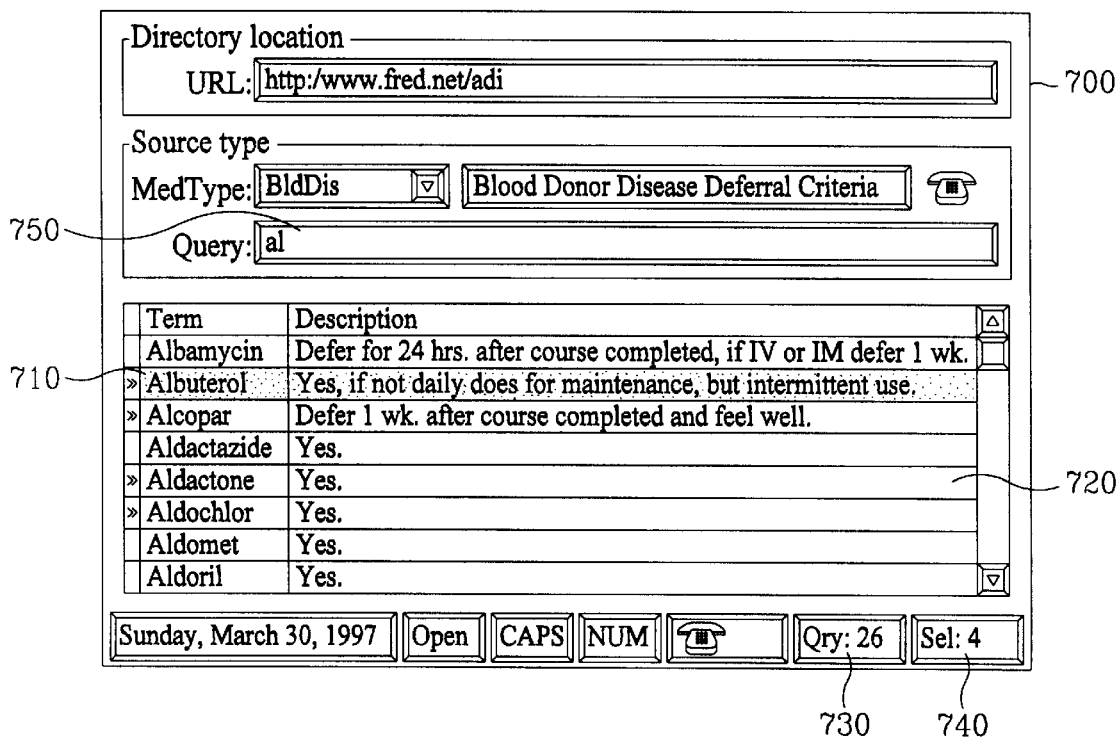
FIG. 7 is an example of a screen of the MedLkUp-client showing the query and display of medical information.

FIG. 7. is an example of a screen 700 showing the screen after the user performs a query and displays the items retrieved, and has also selected items from the display, on the display screen 201 of the MedLkUp-client of FIG. 2. The query criteria is specified by (a.) entering the query criteria into the 'Query' field 750 (b.) pressing the 'Enter' key on the keyboard. This cause the MedLkUp-client program to retrieve from the database all records that meet the query criteria and displaying them in the query grid 720. The retrieved records are displayed in alphabetical order displaying the 'Term' and the 'Description' in the correspondingly labeled fields. The number of records that are selected and displayed is shown in the statusbar panel 730. When more records are retrieved then can be displayed on a single computer screen, a scrollbar appears along the right hand edge of the query grid 720. By pointing at this scrollbar the user causes records that are not displayed to scroll into view, with a similar number of fields that were displayed scrolling out of view. The left-most column of the data grid 720 indicate whether the user has selected the row into a selection set. A symbol '>' 710 is used to indicate that an item has been selected, and its absence to indicate that the item has not been selected. Pointing and clicking at any row in the data grid 720, causes the selection status to toggle—a row to be selected if it is not selected, or a row to be deselected if it has been selected. The number of items in the selection set is indicated by the entry in the statusbar field 740. The contents of the most recent query are displayed on the screen when the field 730 is displayed in 'raised' format and the field 740 shown in a 'flat' format as they appear in FIG. 7. Pointing and clicking at the field 740 causes the field 740 to be shown in 'raised' format, the field 730 to be shown in 'flat' format, and the display grid to show those records that have been selected by the user into the selection set. Subsequently pointing and clicking at the field 730 will cause the field 730 to be shown 'raised', the field 740 to appear 'flat', and the display grid to show those records that have been retrieved by the most recent query. The selection set is not cleared whenever a query is performed as is the query set. This provides a means for the user to select and display records across more than one MedType.

FIG. 8. is an example of a screen 800 showing the screen after the user displays the selection set on the display screen 201 of the MedLkUp-client of FIG. 2. In this figure the statusbar field 810 has been selected by using the mouse pointing device to point and click on this field, causing the MedLkUp-client program to display the contents of the selection set. This field displays the number of items in the selection set, in this case '4'. In addition to the Term and Description column headings displayed on the screen when the query set is displayed, the display grid for the selection set also show the type of medical information, 'MedType' in the Type column 830 of the display grid.

FIG. 9. is an example of a screen 900 showing options that the user may invoke on the query or selection set on the display screen 201 of the MedLkUp-client of FIG. 2. In this figure the popup context menu is displayed whenever the user points anywhere in the display grid 920, and presses the right mouse button. This cause the popup context menu 910 to appear, and the user may select any of the displayed options which will be performed on display grid as it displays either the query set or the selection set. The 'Select All' option select all items on the displayed grid, while the 'DeSelect All' option deselects any items in the grid that have been selected. The 'Clear' option erases all items in the set. If the query set is displayed in the display grid then all items are cleared or removed from the display and the number of items in the set is set to '0' and this number displayed on the statusbar field 940. If the selection set is displayed in the display grid then all items are cleared or removed from the display and the number of items in the set is set to '0' and this number displayed on the statusbar field 930.

Figure 10:
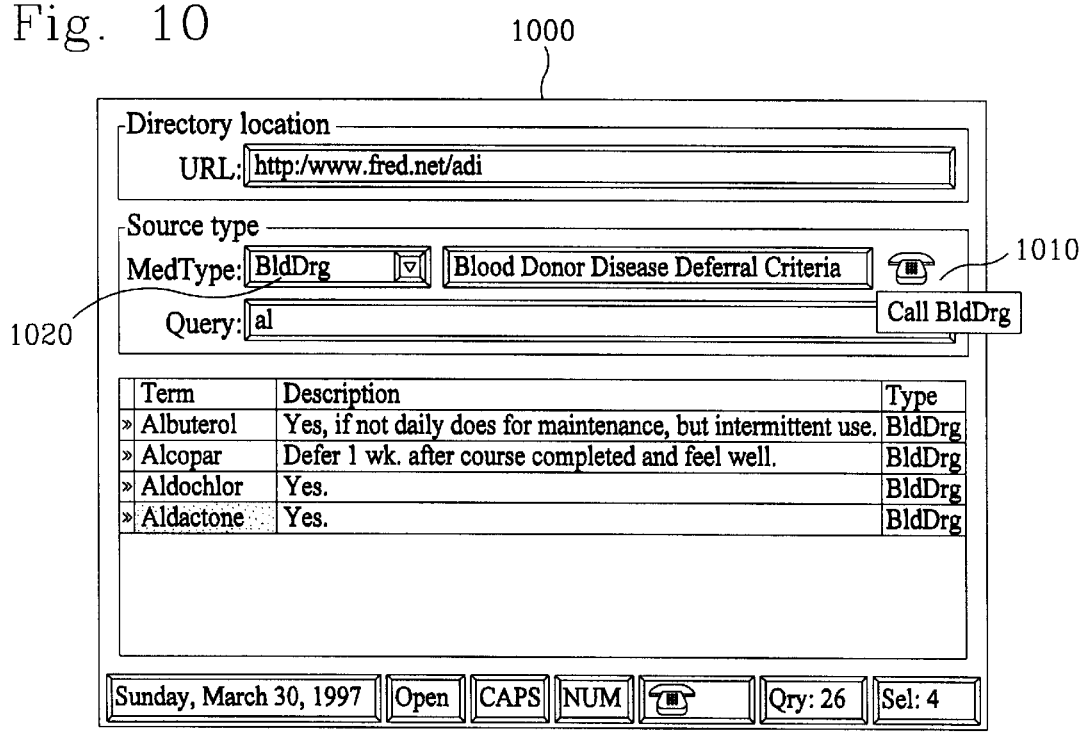
FIG. 10 is an example of a screen of the MedLkUp-client showing how the user initiates a MedCall for assistance.

FIG. 10. is an example of a screen 1000 showing how the user initiates a MedCall for assistance with the MedCall-server for the 'Blood Donor Drug Deferral Criteria' on the display screen 201 of the MedLkUp-client of FIG. 2. The user points and clicks on the telephone icon 1010 with the mouse pointing device. This causes the MedLkUp-client to attempt a MedCall with the MedCall-server associated with the MedType displayed in field 1020.

C. Screen Formats—MedCall-client and MedCall-server

Figure 11:
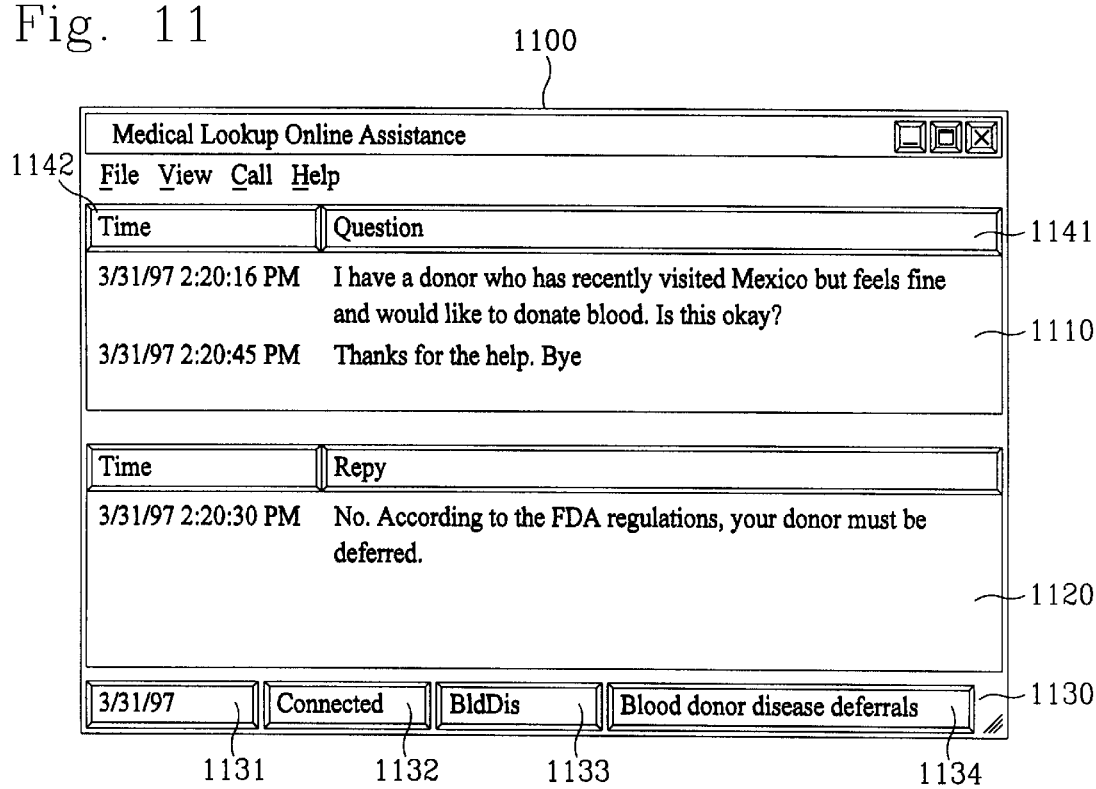
FIG. 11 is an example of a MedCall conversation in split screen view.

FIG. 11 is an example of a screen 1100 that is used by a person on the MedCall-server to engage in a computer conversation with the user of a MedLkUp-client. The identical screen is used in the MedLkUp-client program to allow the user of the MedLkUp-client to engage in the conversation with the expert residing at the MedCall-server site. In the case of the preferred embodiment the functionality of the MedCall-client has been completely subsumed within the MedLkUp-client. In other embodiments however, the MedCall-client program may be a completely separate program. The conversation is shown in what is called split-screen view, in which the top panel 1110 shows the conversation entered by the user on the keyboard of the MedLkUp-client, also called the caller, and the bottom panel displays the conversation entered on the keyboard of the MedCall-server, referred to as the callee. Both the top panel and the bottom panel have two sizable fields. The field 1142 displays the 'Time' at which the fragment of conversation was sent to the other party, and the field 1141 'Question' displays the dialog.

When the screen is shown on the display screen of the MedLkUp-client the cursor which shows the position at which the next keyboard entry will be displayed is focused on the top panel 1110, and always in the last and as yet un-transmitted 'Question' field 1141. When the user of the MedLkUp-client presses the 'Enter' key on the keyboard the typed entry is transmitted over the network to the MedCall-server which displays the entry in the bottom panel 1120.

The system operates symmetrically from the vantage point of the MedCall-server. The user of the MedCall-server type entries which are displayed on the bottom panel 1120 until they press the 'Enter' key at which time the typed entry is transmitted over the network to the MedLkUp-client which displays the entry in the top panel 1110. The 'Time' field is automatically entered whenever the 'Enter' key causes a talk message to pass between the MedLkUp-client and the MedCall-server.

The screen also shows a statusbar 1130 displayed along the bottom of the screen. The status bar has 4 fields. Field 1131 displays the date on which the program was started. Field 1132 identifies whether there is an active set of connections over which the MedLkUp-client and the MedCall-server can implement the computer conversation between the users of the systems. Field 1133 shows the abbreviation of the type of medical information that is being accessed, and field 1134 the full description of the medical information that is being accessed.

FIG. 12 is an example of a screen 1200 that is displayed on the display screen 201 of the MedLkUp-client of FIG. 2. This screen is in dialog view and uses a single panel 1210 to display the conversation between the user of the MedLkUp-client and the person manning the MedCall-server station. The information displayed in dialog view is the same as that in split-screen view of FIG. 11, except that one panel is used to display the entire conversation rather than two panels as in split-screen view.

The user toggles between dialog view and split-screen views by choosing the 'View' option 1230 of the menu by pointing at the 'View' menu option with the mouse pointer device and clicking the button. If the screen is in dialog view then choosing this option changes to split-screen view, while if the screen is in split-screen view, choosing the 'View' menu option changes the screen to display the conversation in dialog view.

In dialog view a new field has been added to the column headers 1220. This field labeled 'Who' identifies the source of the associated dialog. If the dialog is from the 'Caller' then the source of the dialog is the user of the MedLkUp-client, else the source of the dialog is the expert at the MedCall-server site. In the example shown in FIG. 12, there is a short conversation between the user of a MedLkUp-client and the experts at the site providing information about blood donor disease deferral criteria. Such a site would provide expert information about the suggested and mandatory regulations regarding whether a blood donor may donate blood based on their history of disease.

D. Data Structures—MedLkUp-client and MedLkUp-server

FIG. 13 shows the structure of the MedType.1st file that describes the type of medical data that is maintained in the medical definition central database of a MedLkUp-server 300 of FIG. 3. The file has 6 fields the values of which are entered into a single record of the MedType.1st file with each value delimited from the other field values by commas. The first field 1301 is 'MedType' and is a short abbreviation of the type of medical information. The value of this entry should be unique to distinguish the different types of medical information. This field can be no more than 8 characters. The second field 1302 is 'MedTypeDescription' which is a full description of the type of medical information and can be up to 60 characters in length. The third field 1303 is 'MedTypeDefServer' which is the network address of the MedLkUp-server that contains the medical dictionary central database for the associated type of medical database. This field can be up to 128 characters in length. The fourth field 1304 is the 'MedTypeHelpServer' which provides the network address of the MedCall-server that provides the help facility for this type of medical information. The fifth field 1305 is 'MedTypeDateLastUpdated' and provides the date on which the medical dictionary central database was last updated and is in 'dd/mm/yyyy' format. The sixth and last field 1306 in this file is 'MedTypeSource' and is an abbreviated description of the source of the medical information. For instance if the reference source for the information was Food and Drug Administration guidelines then the source might be coded as 'FDA'. This field can be up to 8 characters in length.

FIG. 14 shows an entity relationship (ER) diagram 1400 for the medical dictionary database used on the MedLkUp-client of FIG. 2 and the MedLkUp-server of FIG. 3. There are 2 tables in the database, with the name of each table given at the top of the box representing each table, and below that is a list of the fields in the table. The field names that are highlighted identify the primary key field(s); i.e. the fields that uniquely identify a row of the table. Foreign key relationships between the table are identified by relationship lines drawn between the tables. The label '1' and 'm' on either side of the relationship line indicates that tables have a one-to-many relationship, with many records on the 'm' associated table possibly existing for each unique row of the '1' associated table.

Table MedType 1410 contains information describing a class or type of medical information. The primary key, MedType must have a unique value for each of the types of medical information that the system can address. Two of the more important values in this table are the fields 'MedTypeDefServer' and 'MedTypeHelpServer' which provide the network address of the MedLkUp and MedCall servers for the associated type of data. In the preferred embodiment which uses a TCP/IP network protocol, this is the Uniform Resource Locator (URL) of the servers. The definition and attributes of this table are described in FIG. 15.

In the preferred embodiment each MedLkUp-server can only contain a single type of Medical information and there would only be a single record in the MedType table. In other embodiments however a single server may contain a multiplicity of MedTypes in which case the MedType table would contain one entry for each distinct medical type.

Table MedTerm 1420 contains the medical dictionary terms and their associated definition. The primary key is a combination of the fields 'MedType', 'Term', Predecessor', and 'Patriarch' which are unique even if multiple medical dictionaries are maintained in the same database. The 'Predecessor' and 'Patriarch' fields allow us to fully describe any medical information organized according to a hierarchical structure in the single table MedTerm 1420. The definition and attributes of this table are described in FIG. 15.

In the preferred embodiment each MedLkUp-server can only contain a single type of Medical information and therefore every record in the table MedTerm 1420 would have the same value in the 'MedType'. In other embodiments however a single server may contain a multiplicity of MedTypes in which case the MedTerm table 1420 would contain the definitions for multiple medical dictionaries which are differentiated in the MedTerm table by their value in the field 'MedType'.

FIG. 15 provides the attributes of the table structures 1500 for the medical dictionary database that are presented in the ER diagram of FIG. 14 and which are located on the MedLkUp-client of FIG. 2. and the MedLkUp-server of FIG. 3. The table MedType 1510, contain descriptive information about the type of medical information, the location of the central server and help facility and the date on which the database was last updated. The table MedTerm 1520, contain all medical terms and definitions for a medical dictionary database, including source information and the date on which specific items were last updated.

The fields of table MedType 1510 include MedType 1511, a string of length 8 with the unique abbreviation of the type of medical information; MedTypeDescription 1512, a string of length 60 characters with a full description of the type of medical information; MedTypeDefServer 1513, a string of length 128 characters with the network address of the MedLkUp-server for this type of information; MedType-HelpServer 1514, a string of length 128 with the network address 1514 of the MedCall-server for this type of information; MedTypeDateLastUpdated 1515, a string of length 10 with the date on which the database was last updated and in the format 'dd/mm/yyyy', and MedSource 1516, a string of length 8 with an identifier of the source from which the information in the database was derived.

On the MedLkUp-server the field MedTypeLastUpdated has the latest date on which any entry or revision was made to the local database, while on the MedLkUp-client this field has the latest date on which any entry or revision was made to the local database from the central database. If the value of this field is the same for both the MedLkup client and server systems then it means that the MedLkUp-client database is current with the MedLkUp-server database and does not have to be updated.

The fields of table MedTerm 1520 include MedType 1521, a string of length 8 with the unique abbreviation of the type of medical information; Term 1522, a variable length string of maximum length 32 with the medical term that is being defined; Predecessor 1523, a variable length string of maximum length 32 with the value of the term field for a predecessor term in the categorization hierarchy; Patriarch 1524, a variable length field of maximum length 32 with the value of the term at the top level of the categorization hierarchy; Description 1525, a variable length string of maximum length 255 with the definition of the medical term; Source 1526, a string of length 8 identifying the source of the information, and DateUpdated 1527, a string of length 10 in the format 'dd/mm/yyyy' containing the date on which this item was last updated.

Each row of table MedTerm 1520, completely defines a term in the categorization hierarchy, and its relationship to other items in the hierarchy. The means by which this table models the categorization hierarchy of a medical dictionary is described in Section F. For any individual item, if the value of the DateUpdated field 1527 is more recent on the MedLkUp-server than on the MedLkUp-client then the definition on the MedLkUp-client for this item is out-of-date and must be updated.

E. Data Structures—MedCall

Figures 16, 17:
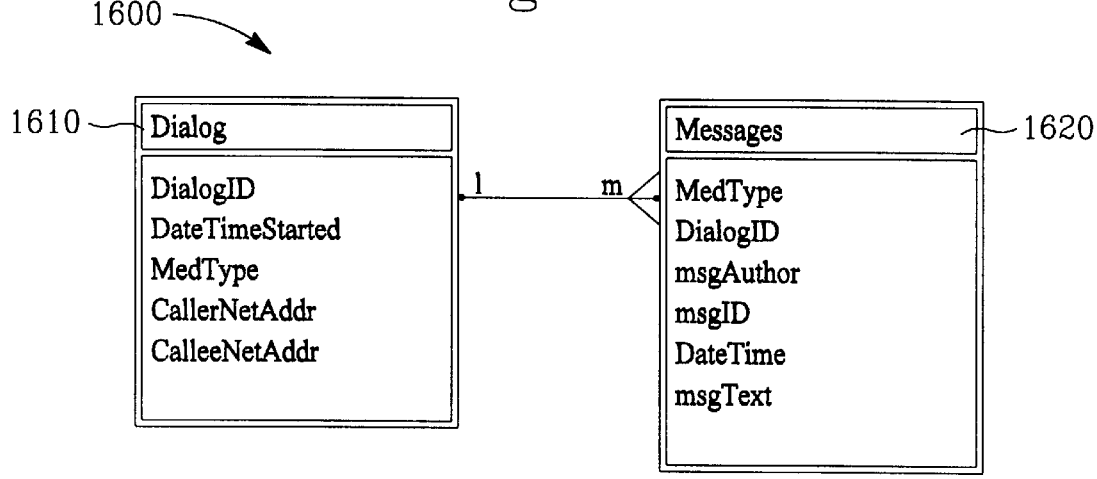
FIG. 16 is an entity-relationship diagram of the MedCall database.
FIG. 17 displays the table structures for the MedCall database.

FIG. 16 shows an entity relationship (ER) diagram 1600 for the MedCall database used on the MedLkUp-client of FIG. 2 and the MedCall-server of FIG. 4. There are 2 tables in the database, with the name of each table given at the top of the box representing each table, and below that is a list of the fields in the table. The field names that are highlighted identify the primary key field(s); i.e. the fields that uniquely identify a row of the table. Foreign key relationships between the table are identified by relationship lines drawn between the tables. The label '1' and 'm' on either side of the relationship line indicates that tables have a one-to-many relationship, with many records on the 'm' associated table possibly existing for each unique row of the '1' associated table.

Table Dialog 1610 contains a single record with information describing each conversation that is carried on between a user of a MedLkUp-client and a person operating the MedLkUp-server and there is one record for each conversation. The primary key 'DialogID' is a unique numeric value for each conversation. The definition and attributes of this table are described in FIG. 17.

Table Messages 1620 contains the full text of all dialog passed as messages between the MedLkUp-client and the MedCall-server. This includes all dialog from both parties to the conversation, and a record of the conversation may be optionally saved on neither, either or both of the MedLkUp-client and MedCall-server sites. The primary key is a combination of the fields 'DialogID', 'msgAuthor', and 'msgId', which uniquely identify every message of every conversation. The definition and attributes of this table are described in FIG. 17.

In the preferred embodiment the MedLkUp-client may access a multiplicity of medical dictionary databases, and so may also access a multiplicity of MedCall-servers. The MedCall database on the MedLkUp-client may therefore contain the dialog of the user of the MedLkUp-client with a multiplicity of different MedCall-servers from the same and or different MedLkUp-client sessions. The MedCall-server will contain the full dialog of conversations with any MedLkUp-clients.

FIG. 17 provides the attributes of the table structures 1700 for the MedCall database that are presented in the ER diagram of FIG. 16 and which are located on the MedLkUp-client of FIG. 2., and the MedCall-server of FIG. 4. The table Dialog 1710, contains descriptive information about each conversation between a user of the MedLkUp-client and an expert at a MedCall-server site. The table Messages 1720, contains a full record of the actual dialog that took place during a MedCall conversation.

The fields of table Dialog 1710 include DialogID 1711, a long integer generated as an increasing sequence number and which uniquely identifies a conversation on the host machine; DateTimeStarted 1712, a string of 16 characters in length in 'dd/mm/yyyy:hh24:mm:ss' format, that gives the date and time on which the conversation was started on the host machine; MedType 1713 a string of 8 characters in length identifying the type of medical information that is the subject of the discussion; CallerNetAddr 1714, a string of up to 128 characters identifying the network address of the user of the MedLkUp-client who has initiated the MedCall, and CalleeNetAddr 1715, a string of up to 128 characters identifying the network address of the MedCall-server. In the preferred embodiment which uses a TCP/IP network protocol, the network address are the Uniform Resource Locator (URL) of the servers.

The fields of table Messages 1720 include DialogID 1721, a long integer identical to an entry in the Table Dialog 1710 identifying the call; msgAuthor 1722, a numeric of length 1 that takes the value 1 if the dialog for the record is generated by the caller on the MedLkUp-client, or a value of 2 if the dialog for the record is generated by the person on the MedCall-server; msgID 1723, a long integer generated as an increasing sequence number and which uniquely identifies dialog within a conversation; DateTime 1724, a string of 16 characters in length in 'dd/mm/yyyy:hh24:mm:ss' format, that gives the date and time on which the message was posted to the MedCall program, and msgText, a variable length string of up to 2000 characters in length that has the text of the dialog.

Each of the MedLkUp-client and the MedCall-server maintain their own copy of the MedCall database. In particular they generate their own counter fields 'DialogID' and 'msgID' as unique identifiers and their own date stamping with 'DateTimeStarted' and 'DateTime' reflecting the time at which the message was posted on the program.

F. Hierarchical structure of a medical dictionary

Figure 18:
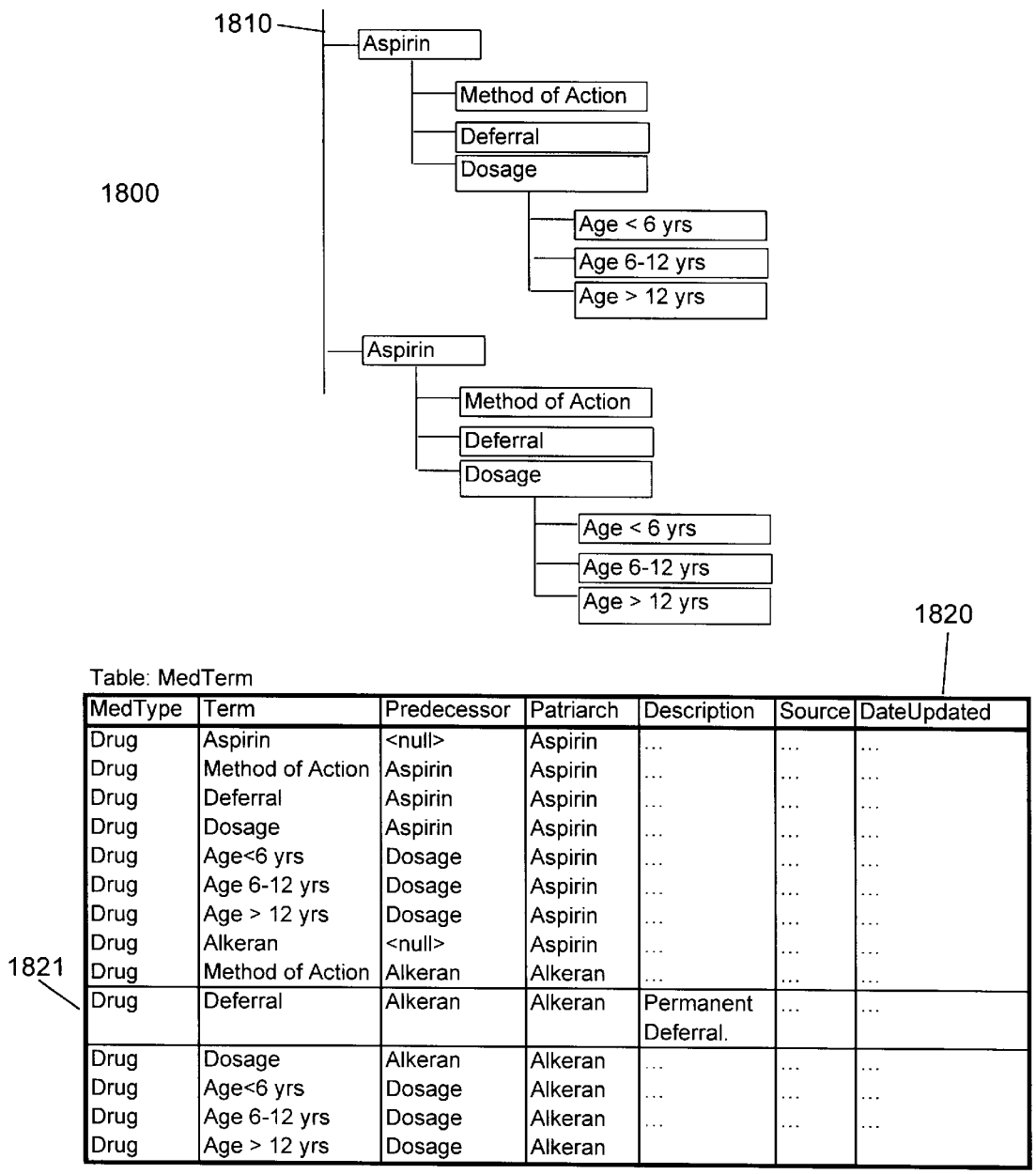
FIG. 18 shows how the MedTerm data table models the categorical hierarchy for a medical dictionary.

FIG. 18 is a diagram 1800 showing how the single table MedTerm 1520 of the MedLkUp database of FIG. 15 can be used to represent a complex hierarchical or tree-like structure.

Such an organization for information is common. For instance a text book may be organized by chapter and section, in which each distinct section would refer to a subset of the information in one and only one chapter, and each chapter refers to a subset of information distinct from any other chapter, but inclusive of all of its sections. We can refer to the level of any item in the information hierarchy as the number which describes the depth of an item in the hierarchy tree, with one being the highest level and numbers greater than one indicating an item that is part of a higher item. In the case of the text book, each chapter would have level one, and each section of a chapter would have a level of two. If a section of the book had further subsections, then these subsections would have level 3.

In the case of medical information about drugs, the highest level may contain the name of the drugs, with a second level identifying different types of information about the drug, such as 'Method of Action', 'Deferral Criteria', and 'Dosage'. For each drug the category 'Dosage' may be further characterized giving the dosage by age ranges.

The tree structure 1810, shows such a possible category hierarchy for a drug database. Two drugs of the tree are shown, Aspirin, and the drug Alkeran. Each drug has a further categorization in this example by 'Method of Action', 'Deferral', and 'Dosage', with the category 'Dosage' being further categorized by 'Age<6 yrs', 'Age 6–12 yrs', and 'Age>12 yrs'.

The coding of this fragment of a tree structure in the MedTerm table is shown in 1820, showing the entries for the corresponding fields 'MedType', 'Term', 'Predecessor', 'Patriarch', 'Description', 'Source', and 'DateUpdated'. For instance row 1821 contains medical information in the field 'Description' indicating that a blood donor is permanently disqualified from donating. The fields 'Term', 'MedType', 'Patriarch', and 'Predecessor' determine that this is 'Deferral' information for the 'Drug' Alkeran, and that it is one of the categories in the hierarchy of 'Alkeran', and its position in the hierarchy of 'Alkeran'.

The 3 fields, 'Term', 'Predecessor', and 'Patriarch' fully describe the relationships among items of the tree, and provide a unique identifier for each item in the tree for a given 'MedType'. Each item in the tree is defined to be at level one of the hierarchy if it has a predecessor set to 'null', else it is a sub-item of some other level of the tree. Any term in the tree is said to have a child relationship to its 'Predecessor' term, if it has a non-null 'Predecessor' term, and the 'Predecessor' is referred to as a parent. A parent can have one or more children, but a child may only have one parent in a hierarchical structure. All items that have the same parent and patriarch have a 'sibling' relationship. With this structure, the table MedTerm may contain the definition of medical terms for an arbitrarily complex hierarchical categorization of the medical information.

In the preferred embodiment the blood donor deferral database has only a single level, and is thus completely described by the field 'Term'—the fields 'Predecessor' and 'Patriarch' add no additional information. In the blood donor disease deferral database, each drug is at the highest level with the associated description providing the description of the deferral criteria. The database may have been alternatively organized with 'deferral' as only one of the categories of information provided for each drug, and as is presented in FIG. 18. In other such embodiments of the invention, in which the medical information may be more finely categorized, the inclusion of predecessor and patriarch fields in the MedTerm table is sufficient to represent the full categorization hierarchy.

G. System state diagram

Figure 19:
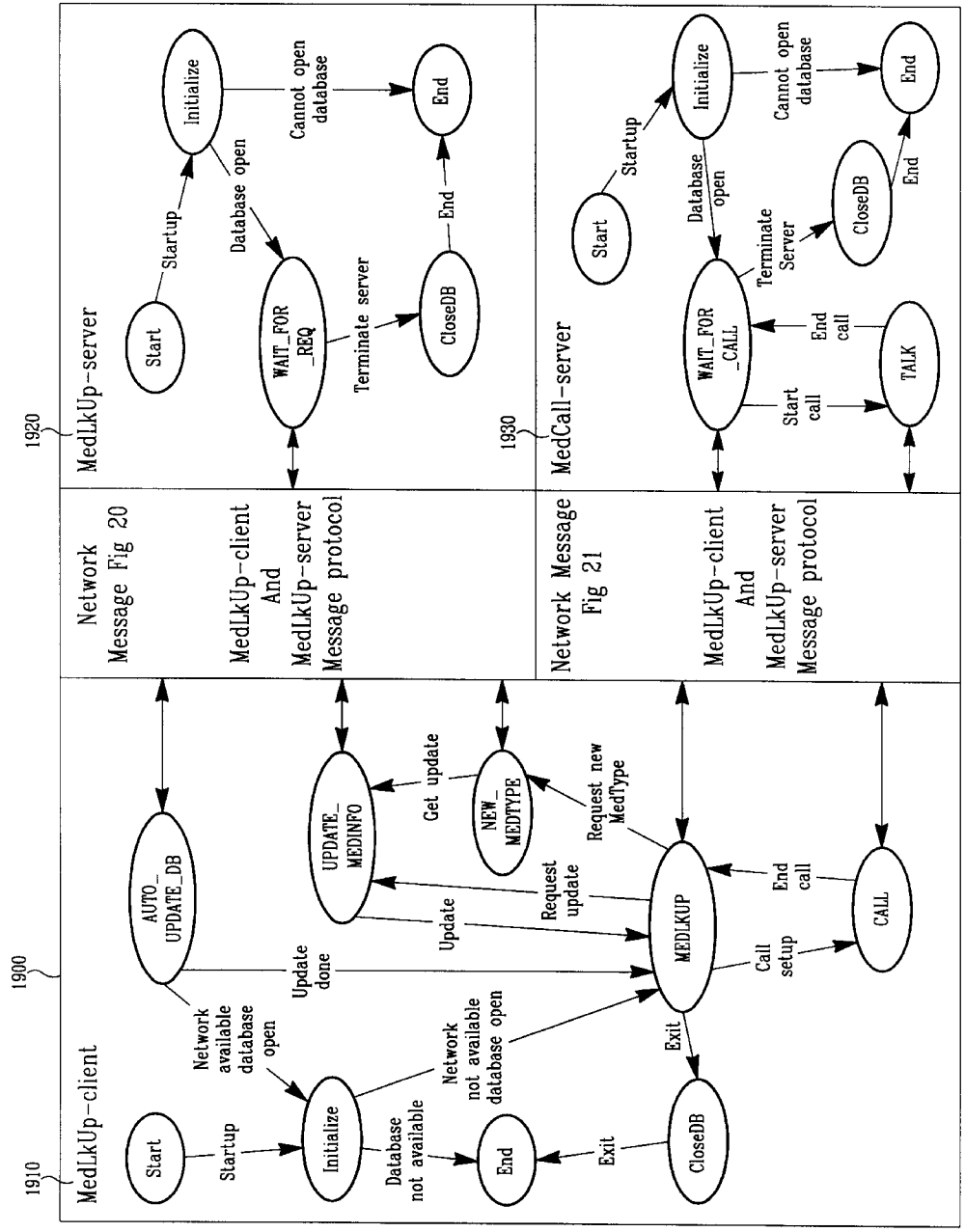
FIG. 19 is a state diagram describing the operation of the MedLkUp-client, MedLkUp-server, and the MedCall-server programs and their interprocess communication messages.

FIG. 19 is a diagram 1900 showing the (1) state machines describing the operation of each of the components of the system (2) the messaging interface between the components of the system. State tables that provide details of the operation of the MedLkUp-client, MedLkUp-server, and MedCall-server are presented in FIGS. 22, 23, and 24 respectively, and details of the message protocols in FIGS. 20 and 21.

FIG. 19 has 5 separate regions. The region labeled MedLkUp-client shows the state machine for the operation of the MedLkUp-client; the region labeled MedLkUp-server shows the state machine for the operation of the MedLkUp-server, and the region labeled MedCall-server shows the state machine for the operation of the MedCall-server. The region labeled 'NetworkMessage FIG. 20' is the network message interface between the MedLkUp-client and the MedLkUp-server and is described in detail in FIG. 20, and the region labeled 'NetworkMessage FIG. 21' is the network message interface between the MedLkUp-client and the MedCall-server and is described in detail in FIG. 21.

The state machine diagrams show the different states that the machine may occur in and the actions which cause them to change state. Arrows pointing to-and-from the NetworkMessage regions show the interprocess communication over the network between the different components of the system, and in particular show which states may send/receive network messages.

The MedLkUp-client state machine 1910 has 9 states. In the state 'START' the program is started and immediately transfers to the state 'INITIALIZE'. State 'INITIALIZE' opens the medical dictionary database, the MedCall database and checks whether the network is available. If either or both databases cannot be opened then the program transfer to the state 'END' and ceases execution. If the databases are open and the network is available then the program transfers to the state 'AUTO_UPDATE_DB' else the program transfers to the 'MEDLKUP' and continues execution.

In the state 'AUTO_UPDATE_DB' the program automatically updates the local medical dictionary database for every medical type that is in the database. This is one of the three state of the MedLkUp-client program that may communicate over the network with the MedLkUp-server program. After the automatic update process if finished the program transfers to the state 'MEDLKUP' to continue processing.

In the state 'MEDLKUP' there are 4 actions that may cause a transfer of program control to another state to continue execution. They are 'CLOSEDB', 'CALL', 'NEW_MEDTYPE', and 'UPDATE_MEDINFO'. The state 'CLOSEDB' signals the program that it will cease execution, and performs this function by transitioning to the state 'CLOSEDB' to close the databases properly and then transition to the state 'END' to terminate the execution of the MedLkUp-client.

The state 'NEW_MEDTYP' occurs when the user enters in a network address of a MedLkUp-server containing a new type of medical information. From this state the program uses the network connection requesting the server to send the MedType.Lis file which contains the definition of the type of medical information, receives and parses the file, and updates the local database. This is the second of the three states of the MedLkUp-client program that may communicate over the network with the MedLkUp-server program. The program then transitions to the state 'UPDATE_MEDINFO' which requests, receives and parses all of the medical information terms and definitions and updates the local database, after which it transitions back to the state 'MEDLKUP' and waits for the user to initiate another action. 'UPDATE_MEDINFO' is the third of the three state of the MedLkUp-client program that may communicate over the network with the MedLkUp-server program. From the state 'MEDLKUP' the user may also request that the local database, for any selected type of medical information, be completely updated from the server database. If the user initiates this action, the program transitions to the state 'UPDATE_MEDINFO' which requests, receives and parses all of the medical information terms and definitions and updates the local database.

From the 'MEDLKUP' state the user may initiate a call over the network to a MedCall-server which results in connections being setup which will be used to carry the MedCall conversation. After the connections are established the program transitions to the state 'CALL' which handles all of the functionality of the call program for the MedLkUp-client. When the MedCall is finished the program terminates the connections and transitions back to the state 'MEDLKUP' to continue processing. The connections between the MedLkUp-client and the MedCall-server are established when a MedCall is setup, and the connection remains active until the call is terminated either by action of either of the parties of the conversation or a network problem occurs.

From the 'MEDLKUP' state the user may also retrieve, select, print and otherwise review and operate on the information from the database.

All of the messages that may be sent from the 'AUTO_UPDATE_DB', 'UPDATE_MEDINFO', and 'NEW_MEDTYPE' states of the MedLkUp-client with the MedLkUp-server persist only for the length of time of the connection; i.e. a message is initiated by opening a connection sending a message and receiving a reply and then closing the connection. All messages that may be sent from the 'MEDLKUP' and 'CALL' states of the MedLkUp-client with MedCall-server are sent over a connection that persists from the time a MedCall is placed until the call is terminated.

The MedLkUp-server state machine 1920 has 5 states. In the state 'START' the program is started and immediately transfers to the state 'INITIALIZE'. State 'INITIALIZE' opens the Medical Dictionary Central database before transferring control. If the database cannot be opened then the program transitions to the state 'END' to perform its termination processing, else it transitions to the state 'WAIT_FOR_REQ' awaiting any network requests for medical information from any MedLkUp-client program.

In the state 'WAIT_FOR_REQ' the MedLkUp-server may receive a network message request from a MedLkUp-client for a MedType.Lis file or a request for medical information. In either case it responds to the request by establishing a network connection, retrieving, formatting and sending the information to the MedLkUp-client, terminating the connection, and then remaining in state to await other network message requests. The server operator may indicate that the MedLkUp-server terminate execution in which case the program transitions to the state 'CLOSEDB' to close the database and then to the state 'END' to finish terminating the execution of the MedLkUp-server.

The state 'WAIT_FOR_REQ' is the only state of the MedLkUp-server that performs communications over the network with the MedLkUp-client. It can receive messages requesting a MedType.list file or that medical information be provided to the requesting MedLkUp-client, and responds to such requests by establishing a network connection, retrieving and formatting the requested information, sending the information, and then terminating the connection.

The MedCall-server state machine 1930 has 6 states. In the state 'START' the program is started and immediately transfers to the state 'INITIALIZE'. State 'INITIALIZE' opens the MedCall database before transferring control. If the database cannot be opened then the program transitions to the state 'END' to perform its termination processing, else it transitions to the state 'WAIT_FOR_CALL' awaiting any network request to setup a call from any MedLkUp-client program.

In the state 'WAIT_FOR_CALL' the MedCall-server may receive a network message request from a MedLkUp-client to provide assistance through a MedCall conversation, in which case it responds by opening up the connections that are used to carry on a conversation. Two connections are established one on which the MedLkup-client talks and the MedCall-server receives, and the second connection over which the MedCall-server talks and the MedLkUp-client receives. If both connections cannot be opened then a call cannot occur and the program remains in the 'WAIT_FOR CALL' state. If both connections are opened successfully then the program transitions to the state 'TALK' to handle all aspects of the conversation. If at anytime during the conversation either of the two network connections is terminated either by design or system fault, then both connections and the MedCall are terminated, and the system transitions from the 'CALL' state back to the state 'WAIT_FOR_CALL' to await the next request for a MedCall from a MedLkUp-client.

The server operator may indicate that the MedCall-server terminate execution in which case the program transitions to the state 'CLOSEDB' to close the database and then to the state 'END' to finish terminating the execution of the MedCall-server.

The states 'WAIT_FOR_REQ', and 'TALK' are the only states of the MedCall-server that performs communications over the network with the MedLkUp-client. Requests to setup a call by establishing the required network connections are processed in the state 'WAIT_FOR_CALL', and all call messaging and the termination of the call and connection are processed in the state 'TALK'.

H. Connection protocol

The preferred embodiment uses an industry standard ethernet and an industry standard TCP/IP network protocol for its computer network. The connection protocol used to handle the access and synchronization of medical information between the MedLkUp-client and MedLkup-server computers is different from the communication protocol used to provide the MedCall feature between the MedLkup-client and MedCall-server computers.

The access and synchronization of medical information between the MedLkUp-client and the MedLkUp-server is implemented by establishing a connection between the computers over the computer network. To minimize computer and network resources for the connection between the MedLkUp-server and the MedLkUp-client, this invention uses a non-persistent network connection; i.e. a network connection is established between the MedLkUp-client and the MedLkUp-server only for the length of time necessary to perform a specific transaction. In the preferred embodiment the connection is implemented using the industry standard hypertext transport protocol (http). In other embodiments the non-persistent connection may be implemented using another industry standard protocol, or a special protocol may be implemented to specifically address operation of a medical lookup information system.

The assistance call feature between the MedLkup-client and MedCall-server computers was implemented by establishing two connections between the MedLkup-client and the MedCall-server. The first connection is used by the MedLkUp-client to send messages to the MedCall-server, and by the MedCall-server to receive messages from the MedLkUp-client. The second connection is used by the MedCall-server to send messages to the MedLkUp-client, and by the MedLkUp-client to receive messages from the MedCall-server. These connections are maintained for the entire length of a conversation about a medical topic and then the call and the connections are terminated; i.e. persist only for the length of an assistance call. Subsequent conversations, even to the same MedCall-server will reestablish a new set of network connections over which to carry the conversation. If either the MedLkUp-client or MedCall-server program terminate either of the connections either by design or another reason, such as network malfunction, the other connection is also caused to terminate and the call ended. In the preferred embodiment the connections are implemented using the industry standard transmission control protocol (tcp) to send and receive the call messages between the MedCall-client and the MedCall-server. In other embodiments the connection may be implemented using another industry standard protocol to transmit the call messages, or a special protocol may be implemented to specifically address operation of the call feature. Other embodiments may also use a different design for the call messages to implement the conversation between the MedCall-client and the MedCall-server.

Figure 20:
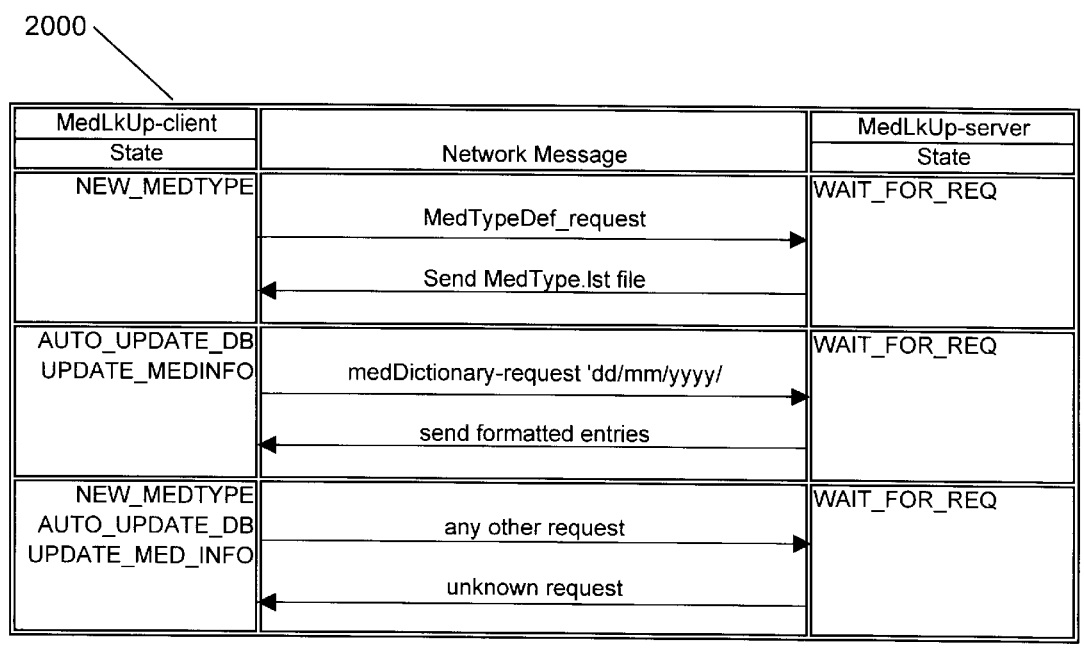
FIG. 20 displays the message protocols for the MedLkUp-client communication with the MedLkUp-server.

FIG. 20 is a diagram 2000 of the network message protocols for communications between the MedLkUp-client and the MedLkUp-server. It shows the MedLkUp-client states on the left side of the figure and the MedLkUp-server states on the right hand side of the figure. The messages that are sent from each state of the MedLkUp-client and their response from the MedLkUp-server are indicated on the diagram.

From state 'NEW_MEDTYPE' a request may be made to the MedLkUp-server for the definition of the type of medical information that the MedLkUp-server maintains. The MedLkUp-server responds by establishing the connection and sending the MedType.1st file after which it terminates the connection.

From either state 'AUTO_UPDATE' or state 'UPDATE_MEDINFO' the MedLkUp-client may request medical information from a MedLkUp-server. The MedLkUp-server responds by establishing the connection, parsing the request for the 'as-of-date' message parameter which is used to define the set of records that has been requested, formatting the reply, sending the information after which it terminates the connection.

From any of the three states 'NEW_MEDTYPE', 'AUTO_UPDATE_DB', or 'UPDATE_MEDINFO' if the MedLkUp-server receives any message other than the previous two messages it responds by establishing the connection, sending the response 'UNKNOWN REQUEST' to the MedLkUp-client and terminating the connection.

FIG. 21 is a diagram 2100 of the network message protocols for communications between the MedLkUp-client and the MedCall-server. It shows the MedLkUp-client states on the left side of the figure and the MedCall-server states on the right hand side of the figure. The messages that are sent from each state of the MedLkUp-client and their response from the MedCall-server are indicated on the diagram.

From state 'MEDLKUP' a request may be made to the MedCall-server to setup a call. The MedCall-server responds by sending the message 'AVAILABLE' if a person is available to engage in the conversation, else it sends the message 'UNAVAILABLE'. If the MedLkUp-server sends any other type of message from the 'MEDLKUP' state, the response will be 'UNKNOWN REQUEST'.

From the state 'CALL' the MedLkUp-client communicates exclusively with the 'TALK' state of the MedCall-server. If the message from the MedLkUp-client to the MedCall-server is to close or terminate the conversation then the network connections are terminated. If the message from the MedCall-server to the MedLkUp-client is to close or terminate the conversation then the network connections are terminated. If the message from the MedLkUp-client to the MedCall-server is client-dialog then the MedCall-server receives the dialog, and if the message from the MedCall-server to the MedLkUp-client is server-dialog then the MedLkUp-client receives the dialog. If the MedLkUp-client or MedCall-server server sends any other message other than close/terminate or dialog, then the receiving system sends the other system the message 'UNKNOWN REQUEST'.

From any of the two states 'MEDLKUP', or 'CALL' if the MedCall-server receives any message other than the previous two messages it responds by establishing the connection, sending the response 'UNKNOWN REQUEST' to the MedLkUp-client and terminating the connection.

I. MedLkUp-client

FIG. 22 is a state table 2200 describing in detail the operation of the MedLkUp-client program. Upon initiation of the MedLkUp-client program it begins in the START state 2210, and then transitions to the state 'INITIALIZE' 2220.

In the 'INITIALIZE' state 2220, if the medical database cannot be opened then the program messages the user 'Database cannot be opened' and transitions to the state 'END' 2290, else if the network connection is available then transition to the state 'AUTO_UPDATE_DB' 2230. If the network is not available the local database can still be used to access medical information so transition to the state 'MEDLKUP' 2240.

In the 'AUTO_UPDATE_DB' state 2230, the MedLkUp-client will automatically update its databases from the medical dictionary central databases on the MedLkUp-servers. For each MedType in the MedType table of the medical database do all of the following items, and when all items are done transition to the state 'MEDLKUP'; (1) open a connection with the MedLkUp-server associated with the MedType—if the connection cannot be opened then write a message on the screen 'Connection could not be opened' and process the next MedType; (2) if the connection is opened successfully then, format a message requesting medical type information with the as-of-date set to the MedTypeDateLastUpdated of the MedType record in the MedType table, send the request message to the appropriate MedLkUp-server and wait for the response; (3) If the response is received successfully then close the connection, begin a transaction, update the medical dictionary entries in the database, update the field MedTypeDateLastUpdated with today's date in the MedType record in the MedType table, and commit the transaction, (4) if the update to the database is not successful then place a message on the display screen 'Could not update database', and rollback the transaction; (5) if the response is not received successfully then close the connection, and place a message on the display screen 'Response not received'.

The state 'MEDLKUP' 2240, handles the user interface for the MedLkUp-client. In this state, the MedLkUp-client idles waiting for one of two actions to occur; an 'Initialize' action 2241, which initializes the screen form when the screen is first displayed to the user, or a 'User-request' action 2242 which includes all of the actions the user may take with the program through the MedLkUp-client user interface.

If the requested action is 'Initialize' 2241, then the program fills the MedType combo box on the display screen with the values of all MedType in the local database, the QueryGrid is displayed with no records in it, set a variable identifying whether the QueryGrid or the SelectGrid is displayed to 'QueryGrid', select the currentMedType as the first entry in the MedType combo box and continue processing.

If the requested action is 'User-request' 2242, then the program processes the 'User-request'. The choices for the 'User-request' are 'SELECT-MEDTYPE', to change the selection of the type of medical information to review from the database; 'SELECT_QUERY_GRID' to choose the QueryGrid as the type of data displayed; 'SELECT_SELECTION_GRID' to choose the SelectGrid as the type of data displayed; 'KeyEnter' to handle user entered keystrokes from the keyboard; 'CLEAR' to clear the contents of the grid that is currently displayed; 'PRINT' to print the contents of the grid that is currently displayed; 'CALL' to initiate a call to the MedCall-server for the selected MedType; 'UpdateMedType' to update the contents of the medical database for a type of medical information identified by the value in the MedType combo box with the medical information on the MedLkUp-server associated with that MedType, or 'Exit' to terminate the execution of the program.

The User-request 'SELECT_MEDTYPE' is performed by using the mouse pointing device to select an item from the MedType combo box, causing the program to change the selected item. The User-request 'SELECT_QUERY_GRID' is performed by using the mouse pointing device to choose the query grid by pointing at the panel that displays the number of rows in the query grid and labeled 'Qry' from the statusBar along the bottom of the MedLkUp-client screen, causing the program to display the QueryGrid. The User-request 'SELECT_SELECTION_GRID' is performed by using the mouse pointing device to choose the query grid by pointing at the panel that displays the number of rows in the query grid and labeled 'Sel' from the statusBar along the bottom of the MedLkUp-client screen, causing the program to display the SelectGrid.

The User-request 'KeyEnter' is performed by entering a keystroke on the keyboard of the MedLkUp-client. If the selected display screen field is the QueryField then this operation will build or execute a query for medical information from the database, and if the selected display screen field is the URL field then this operation will build or execute a request for a new type of medical information.

If the selected field is the QueryField then check if the key that is entered is the 'ENTER' key, and if it is then; (1) Display and clear the QueryGrid; (2) perform the search on the database using the current value of MedType and the value of the QueryField; (3) display the results in the QueryGrid. If it is not the 'ENTER' key then add the key that was entered to the current field.

If the selected field is the URL field then check if the key that is entered is the 'ENTER' key, and if it is then; (1) set the newMedTypeServer field to the value of the URL field, set the asofdate to 'Jan. 1, 1950' to get all entries in the database, and transition to the state 'NEW_MEDTYPE', and if it is not the 'ENTER' key then add the key that was entered to the URL field.

The User-request 'CLEAR' is performed by using the mouse pointer device to point to the displayed grid, choosing the right mouse button to bring up a popup menu and selecting the 'CLEAR' option from the popup menu, causing the program to clear the contents of the currently displayed grid.

The User-request 'PRINT' is performed by using the mouse pointer device to point to the displayed grid, choosing the right mouse button to bring up a popup menu and selecting the 'PRINT' option from the popup menu, causing the program to print the contents of the currently displayed grid.

The User-request 'CALL' is performed by using the mouse pointer to point to the telephone icon, and selecting it with the left mouse button. There are two telephone icons. The telephone icon next to the MedType field is used to begin a MedCall to the MedCall-server that supports the specific type of data identified by the selected MedType, while the telephone icon on the statusBar is used to begin a MedCall with a MedCall-server that is general for the site.

In the present embodiment the specific telephone icon would be use to place a MedCall with a site that is expert in how the presence or history of disease would affect blood donation deferrals, while the general site might be to the blood center medical director.

Whichever telephone icon is chosen the first action that is taken is to check if the network is available, and if it is not then message the user 'Network not available' and no call can be placed. If the network is available then send a request to the MedCall-server to establish a connection and transition to the state 'CALL' 2270.

The User-request 'UpdateMedType' is performed by using the mouse pointer to point to the combo box MedType, choosing the right mouse button to bring up a popup menu and selecting the 'UPDATE' option from the popup menu, causing the program to transition to the state 'UPDATE_MEDINFO' 2260, and set the as-of-date parameter to 'Jan. 1, 1950', which will select all items in the central database.

The User-request 'Exit' is performed by using the mouse pointer to point at the combobox MedType, choosing the right mouse button to bring up a popup menu and selecting the 'EXIT' option from the popup menu, causing the program to transition to the state 'CLOSEDB'.

In the 'NEW_MEDTYPE' state 2250, the MedLkUp-client will attempt to add a new type of medical information to the local database and update the database with the most current information. First the MedLkUp-client will request a connection with the MedLkUp-server at the newMedTypServer site. If the connection cannot be opened successfully then a message 'Connection could not be opened' is displayed for the user. If the connection is established then; (1) format a request-msg requesting the MedLkUp-server to send the MedType.1st file; (2) send the request-msg and wait for the response; (3) if the response-msg is received successfully then close the connection, begin a new database transaction, update the database, commit the transaction and transition to the state 'UPDATE_MEDINFO' 2260.

In the state 'UPDATE_MEDINFO' 2260, the MedLkUp-client will update the local medical dictionary database with entries from the database on the MedLkUp-servers using the value of the asof-date parameter. First the MedLkUp-client will request a connection. If the connection cannot be opened successfully then a message 'Connection could not be opened' is displayed for the user. If the connection is established then; (1) format a request-msg using the asof-date parameter set to 'Jan. 1, 1950'; (2) send the message to the MedLkUp-server and wait for the response; (3) receive the response and terminate the connection (4) begin a new transaction (5) update the medical dictionary database (6) commit the transaction and transition to the state 'MEDLKUP' 2240.

In the state 'CALL' 2270 the MedLkUp-client uses the network to contact and participate in a key-entered typed conversation with persons located at a MedCall-server site. In this state the MedLkUp-client idles waiting for one of three actions to occur; 'StartCall' 2271 when the MedCall screen on the client side is started; 'NetworkMessage' 2272 to respond to a network message, or 'User Action' 2273, to handle the user interface with the user during a MedCall.

If the requested action is 'StartCall' 2271, which occurs only when the MedCall screen is first displayed, the MedCall screen is displayed in split screen view, the msgbuffer is cleared, and a message is written to the MedCall database indicating a MedCall has begin.

If the requested action is 'NetworkMessage' 2272 then it is an incoming message so we retrieve and parse the message. If the message is not a talk-msg then ignore it, else display the message on the screen in the 'callee' screen, and write the message to the MedCall database.

If the requested action is a 'User Action', 2273 then we must identify the type of user-request and act accordingly. There are five different type of user request; 'KeyPressed' handling keyboard entries by the user, 'PRINT' to print the MedCall dialog, 'SPLITSCREEN' to display the dialog in split screen view, 'DIALOGSCREEN' to cause the program to display the dialog in dialog view, and 'EXIT' or 'BYE' to terminate the MedCall.

If the user request is 'KeyPressed' then we either send the contents of the msgbuffer to the MedCall-server if the key that has been pressed is the 'ENTER' key, or else add the key to the msgbuffer and display it. If the key is 'ENTER' then send the msgbuffer to the MedCall-server, write the msgbuffer to the dialog database, and clear the msgbuffer for the next message.

If the user request is 'PRINT' then the entire conversation by both parties is printed on the system printer.

If the user request is 'SPLITSCREEN' then the conversation is displayed in split screen view which displays the 'caller' and 'callee' dialog in separate panels.

If the user request is 'DIALOGSCREEN' then the conversation is displayed in dialog screen view which displays the 'caller' and 'callee' dialog in the same panel in temporal order.

If the user request is 'EXIT' or 'BYE' then the connection with the MedCall-server is terminated, write an end-message to the MedCall database, commit all dialog to the database, terminate the MedCall and transition to the state 'MEDLKUP' 2240.

In the 'CLOSEDB' state 2280 the MedLkUp-client closes the medical dictionary database, and the MedCall database, and transitions to the state 'END'.

In the 'END' state 2290, the MedLkUp-client terminates execution of the MedLkUp-client program.

J. MedLkUp-server

FIG. 23 is a state table 2300 describing in detail the operation of the MedLkUp-server program. Upon initiation of the MedLkUp-server program it begins in the START state 2310, and then transitions to the state 'INITIALIZE' 2320.

In the 'INITIALIZE' state, if the medical dictionary central database cannot be opened then the program messages the operator 'Database cannot be opened' and transitions to the state 'END' 2350, else if the database is opened successfully then it transitions to the state 'WAIT_FOR_REQ' 2330.

In the 'WAIT_FOR_REQ' state 2330, the MedLkUp-server idles waiting for one of two actions to occur; a NetworkRequest action 2331, indicating a network message has been received and must be acted upon, or a Terminate-Server action 2332, to terminate the operation of the server.

If the requested action is TerminateServer then we transition to state 'CLOSEDB' 2340.

If the requested action is a NetworkRequest then the server establishes the connection with the MedLkUp-client and then checks the type of request message. If the message is (1) a request for the type of medical information that the server maintains then the server sends the MedType.1st file to the MedLkUp-client; else if the message is (2) a request for medical dictionary entries then the program parses the message to get the asof-request-date, retrieves and formats the response message for all entries in the database entered or updated since the asof-request-date and, sends the entries in a response message to the MedLkUp-client or for (3) any other message, ignore the message and send the response message 'UNKNOWN REQUEST' to the MedLkUp-client. After the response message is sent, terminate the connection and continue to wait for a requested action in the state 'WAIT_FOR_REQ'.

In the 'CLOSEDB' state 2340, the MedLkUp-server closes the medical dictionary central database and transitions to the state 'END'.

In the 'END' state 2350, the MedLkUp-server terminates execution of the MedLkUp-server program.

K. MedCall-server

FIG. 24 is a state table 2400 describing in detail the operation of the MedCall-server program. Upon initiation of the MedCall-server program it begins in the START state 2410, and then transitions to the state 'INITIALIZE' 2420.

In the 'INITIALIZE' state, if the MedCall database cannot be opened then the program messages the operator 'Database cannot be opened' and transitions to the state 'END' 2460, else if the database is opened successfully then set NumLiveCall=0, MedInfoSpecialistAvailable=true, and transitions to the state 'WAIT_FOR_CALL' 2430.

In the 'WAIT_FOR_CALL' state 2430, the MedCall-server idles waiting for one of four actions to occur; a NetworkRequest 2431, indicating a network message has been received and must be acted upon, a SetOpsUnavailable action 2432 informing the server to reject all incoming network messages, a SetOpsAvailable action 2433 informing the server to accept and process incoming network, or a TerminateServer action 2434 to terminate the operation of the server.

If the requested action is a NetworkRequest 2431, then the server establishes the connection with the MedLkUp-client and then checks the type of request message. If the message is (1) to establish a MedCall then write the message to the MedCall database and establish the connections with the MedLkUp-client; else if it is any other message then discard the message, and send the response 'UNKNOWN REQUEST' to the MedLkUp-client.

Next check if MedInfoSpecialistAvailable=false then send the response 'UNAVAILBABLE' to the MedLkUp-client, write 'OPSUNAVAILABLE' to the MedCall database and terminate the network connection; else if MedInfoSpecialist=true then send the response 'AVAILABLE' to the MedLkUp-client, write 'OPSAVAILABLE' to the MedCall database, set MedInfoSpecialistAvailable= false, set NumLiveCalls=1, initialize the talk buffer by setting TalkBuffer="", a null string, and transition to the state 'TALK' 2440.

If the requested action is 'SetOpsUnavailable' 2432, then if the value of MedInfoSpecialistAvailable=true then set MedInfoSpecialistAvailable=false.

If the requested action is 'SetOpsAvailable' 2433, then if the value of MedInfoSpecialistAvailable=false then set MedInfoSpecialistAvailable=true.

If the requested action is 'TerminateServer' 2434, then transition to the state 'CLOSEDB' 2450.

In the 'TALK' state 2440, the MedCall-server idles waiting for one of five actions to occur; a NetworkRequest 2441, indicating a network message has been received and must be acted upon, a KeyPressed action 2442 indicating the user has entered a keystroke on the keyboard, a SetOpsUnavailable action 2443 informing the server to reject all incoming network messages, a SetOpsAvailable action 2444 informing the server to accept and process incoming network, or a TerminateServer action 2445 to terminate the operation of the server.

If the requested action is 'NetworkRequest' 2441, then (1) if the request is to close the connection then write a close connection message to the MedCall database and to the client panel on the screen, close the connections, set MedInfroSpecialistAvailable=true, set NumopenLines=0, then clear the client pane and server panel on the display screen of all dialog, and transition to the state 'WAIT_FOR_CALL' 2430, else (2) if the request is a talk message then write the talk message to the client panel on the display screen, and write the talk message to the MedCall database, else (3) if the request message is to terminate the call then write a close connection message to the MedCall database and to the client panel on the screen, close the connections, set MedInfroSpecialistAvailable=true, set NumOpenLines= 0, then clear the client panel and server panel on the display screen of all dialog, and transition to the state 'WAIT_FOR_CALL' 2430, else (4) if the message is any other message then disregard the message.

If the requested action is 'KeyPressed' 2442, then (1) if the key that was entered is the 'ENTER' key then send the talkbuffer to the MedLkUp-client, write the talkbuffer to the MedCall database, and reset the talkbuffer to "", the null string, else (2) if the key is any other key then add it to the end of the talkbuffer.

If the requested action is 'SetOpsUnavailable' 2443, then if the value of MedInfoSpecialistAvailable=true then set MedInfoSpecialistAvailable=false.

If the requested action is 'SetOpsAvailable' 2444, then if the value of MedInfoSpecialistAvailable=false then set MedInfoSpecialistAvailable=true.

If the requested action is 'TerminateServer' 2445, then send a terminate message to the MedLkUp-client and write a terminate message to the MedCall database, close the connections, and transition to the state 'CLOSEDB' 2450.

In the 'CLOSEDB' state 2450, the MedCall-server closes the MedCall database and transitions to the state 'END'.

In the 'END' state 2460, the MedCall-server terminates execution of the MedCall-server program.

3. Other Embodiments

Other embodiments of the inventions use the same principles to implement a system that provides access to medical information over a network. In the preferred embodiment the type of information stored on a medical dictionary central database of a MedLkUp-server is defined in a file MedType.1st which is transmitted to the MedLkUp-client and which specifically formatted information. In other embodiments other means may be used to transmit this information and other information may be necessary to describe its contents. In the preferred embodiment only two MedLkUp-servers were used, one to provide blood donor deferral information for diseases and the other for drugs, but in other embodiments additional MedLkUp-server medical dictionaries may be part of the system providing access to other types of medical information.

In the preferred embodiment each MedLkUp-server contains a single type of medical information in the medical dictionary central database, but in other embodiments a single MedLkUp-server may serve a multiplicity of types of medical information. This could be implemented in many different ways such as expanding the definition of the MedType.1st file to have one record for each type of medical information the MedLkUp-server supports and including the type of medical information in the network messages between the MedLkUp-client and the MedLkUp-server.

The medical dictionary database used in the preferred embodiment were particularly simple having only two levels, medical type, and then medical term. Other embodiments can use the same database structure to contain information for a medical dictionary database that follows a hierarchical structure and whose complexity, as measured by levels, can be any number greater than two. Such information would include cancer or other disease treatment protocols, federally regulated material safety data sheets, commonly referred to by the abbreviation (MSDS), and drug reaction information, and blood and plasma center Standard Operating Procedures (SOPS), or an SOP for any organization. This list is not exhaustive but only provides examples of the kinds of medical information, that can be organized according to a hierarchical or tree structure, that the present system can handle.

In the preferred embodiment, requests by the MedLkUp-client for service by the MedLkUp-server are formatted according to the industry standard common gateway interface protocol. In other embodiments, the formatting of the request may be by another messaging protocol.

In the preferred embodiment, the information retrieved from the database is all of a textual format, but in other embodiments the information in the database may be expanded to include other objects such as pictures, audio, or video.

In the present embodiment the date/time stamp of entries in the medical database is a date. In other embodiments this may be expanded to include also the time at which the data was added or updated.

Still in other embodiments there may be additional options that the user may use to determine how frequently a database is updated over the network. In the present embodiment the database is updated whenever the MedLkup-client program is started and the network is available. Another option would be update the database after 30 day have elapsed since the last update. This would be a common situation in which the application of medical information follows regulatory or SOP guidelines which require that new medical information be incorporated within 30 days of being released or posted. Other embodiments may provide the user with options to update the database more or less frequently than the preferred embodiment.

Still in other embodiments some means such as version number may be used to indicate when an item of medical information needs to be updated in the local database.

Still in other embodiments the MedCall facility may be implemented to run over a single connection rather than two connections so that the client-conversation and the server-conversation both use the same connection for communication. Alternatively the MedCall facility may be implemented so that it sends the conversation dialog more frequently than in the preferred embodiment which uses the 'ENTER' key to signal the program to transmit the dialog. In the preferred embodiment the MedCall-server can handle only one conversation at a time with a user of a MedLkUp-client. In other embodiments however, the MedCall-server can have a multiplicity of persons manning MedCall stations, and the MedCall-server will keep track of which persons are available and route conversation between the MedLkUp-client requiring service with one of the persons at the MedLkUp-server site providing assistance.

Other embodiments will be apparent to those skilled in the art from consideration of the specification and practice of the invention disclosed herein. It is intended that the specification and examples be considered as exemplary only, with a true scope of the invention being indicated by the following claims.

What is claimed is:

1. A computer system to look up and access medical information over a computer network comprising:

a client program referred to as a medLkUp-client;

a server program referred to as a medLkUp-server;

in which the medLkUp-client can establish and terminate a connection over the computer network to the medLkUp-server and send and receive data;

in which the medLkUp-server can establish and terminate a connection over the computer network to the medLkUp-client and send and receive data;

in which medical information is categorized according to the type of medical information, referred to as its medical type;

in which the medical information for each medical type can be organized in a hierarchical structure;

in which medical information is stored in a database, referred to as a medical dictionary;

in which for each medical type there is a central reference medical database accessible on a network database server, referred to as the medical dictionary central database;

in which for each medical type there is a medical type definition which describes the type of medical information contained in the medical dictionary, and where it is located;

wherein medLkUp-server contains a medical type definition of the type of medical information it stores, and a medical dictionary central database with the corresponding medical database;

wherein the medLkUp-server program can be started and stopped; and wherein the medLkUp-server program responds to a request from a medLkUp-client for a medical type definition by (a) establishing the connection with the medLkUp-client, (b) retrieving the medical type definition, (c) sending the medical type definition to the medLkUp-client, and (d) terminating the connection.

2. The system of claim 1 in which the medLkUp-client contains a local database with the medical type definition for each different type of medical information it stores, and the medical dictionary for each different type of medical information it stores.

3. The system of claim 2;

in which the medLkUp-client has the means to specify the network location of a medLkUp-server;

in which the medLkUp-client program has the means to request the medical type definition from a medLkUp-server;

in which the medLkUp-client program has the means to receive a medical type definition from a medLkUp-server;

in which the medLkUp-client program has the means to parse and store in its local database the medical type definition received from the medLkUp-server.

4. The system of claim 3 in which the medLkUp-client program has the means access a medical type definition from a medLkUp-server and store it in its local data by (a.) establishing a connection with the MedLkUp-server over the network (b.) requesting the medical type definition from the medLkUp-server (c.) receiving the medical type definition from the medLkup-server; (e.) terminating the network connection (f.) parsing and, updating or appending the medical type definition in its local database.

5. The system of claim 2;
in which the medLkUp-client program has the means to request new and revised medical information from the medLkUp-server;
in which the medLkUp-client program has the means to receive new and revised medical information from the medLkUp-server;
in which the medLkUp-client program has the means to parse and store the new and revised medical information received from the medLkUp-server;
in which the medLkUp-client program has the means to save the date on which the medical information was last updated in the local database.

6. The system of claim 5 in which the medLkUp-client program can update the medical information for a medical type in its local database by (a.) establishing a connection with the MedLkUp-server over the network (b.) retrieving the date from the local database on which the medical type was last updated in the local database (c.) requesting all new and revised medical information from the medLkUp-server since the date on which the medical type was last updated in the local database (d.) receiving the information from the medLkUp-server; (e.) terminating the network connection (f) parsing and updating or appending the medical information in the local database.

7. The system of claim 6 in which, whenever the MedLkUp-client program is started, it will automatically update the medical information for each type of medical information in its local database.

8. The system of claim 2;
in which the user of the medLkUp-client program has the means to build a search criteria, and execute the search criteria to retrieve items from the local database that meet the search criteria;
in which the user of the medLkUp-client program has the means to select the type of medical information that will be used in the search criteria;
in which the user of the medLkUp-client program has the means to enter a search term to be used in the search criteria;
in which the user has the means to cause the medLkUp-client program to search for all items in the medical dictionary that meet the search criteria;
in which the medLkUp-client program has the means to display the results of a search;
in which the medLkUp-client program has the means to access, select, display and otherwise use the medical information displayed as the result of a search.

9. A computer system to look up and access medical information over a computer network comprising:
a client program referred to as a medLkUp-client;
a server program referred to as a medLkUp-server;
in which the medLkUp-client can establish and terminate a connection over the computer network to the medLkUp-server and send and receive data;
in which the medLkUp-server can establish and terminate a connection over the computer network to the medLkUp-client and send and receive data;
in which medical information is categorized according to the type of medical information, referred to as its medical type;
in which the medical information for each medical type can be organized in a hierarchical structure;
in which medical information is stored in a database, referred to as a medical dictionary;
in which for each medical type there is a central reference medical database accessible on a network database server, referred to as the medical dictionary central database;
in which for each medical type there is a medical type definition which describes the type of medical information contained in the medical dictionary, and where it is located;
wherein medLkUp-server contains a medical type definition of the type of medical information it stores, and a medical dictionary central database with the corresponding medical database;
wherein the medLkUp-server program can be started and stopped; and
wherein the medLkUp-server program responds to a request from a medLkUp-client for new and revised medical information from the medical dictionary central database by (a) establishing the connection with the medLkUp-client, (b) parsing the message from the medLkUp-client to get the date to use in determining currency of the information, (c) retrieving all records from the medical dictionary central database that have been added or revised since that date, (d) sending the retrieved medical information to the medLkUp-client, and (e) terminating the connection.

10. A computer system to look up and access medical information over a computer network comprising:
a client program referred to as a medLkUp-client;
a server program referred to as a medLkUp-server;
in which the medLkUp-client can establish and terminate a connection over the computer network to the medLkUp-server and send and receive data;
in which the medLkUp-server can establish and terminate a connection over the computer network to the medLkUp-client and send and receive data;
in which medical information is categorized according to the type of medical information, referred to as its medical type;
in which the medical information for each medical type can be organized in a hierarchical structure;
in which medical information is stored in a database, referred to as a medical dictionary;
in which for each medical type there is a central reference medical database accessible on a network database server, referred to as the medical dictionary central database;
in which for each medical type there is a medical type definition which describes the type of medical information contained in the medical dictionary, and where it is located;
wherein the medLkUp-client contains a local database with the medical type definition for each different type of medical information it stores, and the medical dictionary for each different type of medical information it stores;
wherein the medLkUp-client program has means to request new and revised medical information from the medLkUp-server;
in which the medLkUp-client program has means to receive new and revised medical information from the medLkUp-server;

in which the medLkUp-client program has means to parse and store the new and revised medical information received from the medLkUp-server;

in which the medLkUp-client program has means to save the date on which the medical information was last updated in the local database;

in which the medLkUp-client program can update the medical information for a medical type in its local database by (a) establishing a connection with the medLkUp-server over the network, (b) retrieving the date from the local database on which the medical type was last updated in the local database, (c) requesting all new and revised medical information from the medLkUp-server since the date on which the medical type was last updated in the local database, (d) receiving the information from the medLkUp-server, (e) terminating the network connection, and (f) parsing and updating or appending the medical information in the local database; and wherein the user can choose to completely replace all medical information in its local database by (a) establishing a connection with the medLkUp-server over the network, (b) requesting all new and revised medical information from the medLkUp-server using any date prior to when the database was established, (c) receiving the information from the medLkUp-server, (d) terminating the network connection, (e) deleting all medical information of this medical type from the local database, and (f) parsing and appending the medical information in the local database.

11. A computer system for enabling a client to look up and access medical information over a computer network, the computer system comprising:

a client computer including a medical lookup client program (MedLkUp-client) stored in a memory thereof;

a plurality of medical computer servers each including a medical lookup server program (MedLkUp-server) stored in a memory thereof, wherein each of said medical computer servers includes a central database for a different type of medical information so that a first one of said medical computer servers includes a central database for a first type of medical information, a second of said medical computer servers includes a central database for a second type of medical information not including said first type of medical information, and a third of said medical computer servers includes a central database for a third type of medical information not including said first and second types of medical information;

said client computer and said plurality of medical computer servers communicating with one another over the computer network;

wherein said client computer includes a local database of medical information for a multiplicity of different types of medical information, and wherein said client computer automatically updates itself with updated medical information from a plurality of said medical computer servers;

said client computer and medical lookup client program for enabling a user of the client computer to select medical information search criteria and retrieve information from the local database which meets said criteria and to request additional medical information from medical computer servers;

wherein each of said medical computer servers responds to requests from the client computer for medical information stored in said server by retrieving the medical information requested by the client computer from a memory in said server and sending the retrieved medical information to said client computer via said computer network;

wherein for each of a plurality of medical information types there is a central reference medical database accessible on one of said servers, and for each of said medical information types there is an identification for identifying a server or address where that particular medical information type is located; and wherein said client computer accesses a plurality of said medical computer servers over said computer network in order to add new types of medical information to said local database of said client computer.

12. The computer system of claim 11, further including a MedCall-server in communication with said client computer over said network, said MedCall-server including means for enabling a user of the client computer to engage in a real-time keyboard-entered and typed conversation over said network between the user and a person at a help site who can provide expert assistance to the user.

* * * * *